US006794512B2

(12) United States Patent
Shavnya et al.

(10) Patent No.: US 6,794,512 B2
(45) Date of Patent: Sep. 21, 2004

(54) EFFICIENT SYNTHESIS OF 5-HETEROATOM-CONTAINING -PYRAZOLES

(75) Inventors: Andrei Shavnya, East Lyme, CT (US); Subas M. Sayka, East Lyme, CT (US); Martha L. Minich, Gales Ferry, CT (US); Bryson Rast, Mystic, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/285,836

(22) Filed: Nov. 1, 2002

(65) Prior Publication Data
US 2003/0139407 A1 Jul. 24, 2003

Related U.S. Application Data
(60) Provisional application No. 60/335,687, filed on Nov. 2, 2001.

(51) Int. Cl.⁷ .................. C07D 231/24; C07D 235/065; C07D 401/04
(52) U.S. Cl. .................... 546/276.1; 544/182; 544/238; 544/405; 548/370.1
(58) Field of Search ................................ 544/182, 238, 544/405; 546/276.1; 548/370.1

(56) References Cited

FOREIGN PATENT DOCUMENTS

| EP | 1104758 | 6/2001 | ......... C07D/401/04 |
| EP | 1104759 | 6/2001 | ......... C07D/405/14 |
| EP | 1104760 | 6/2001 | ......... C07D/405/14 |
| WO | WO 9711704 | 4/1997 | ......... A01K/31/635 |
| WO | WO 0140216 | 6/2001 | ......... C07D/401/04 |
| WO | WO 0164669 | 9/2001 | ......... C07D/401/04 |

OTHER PUBLICATIONS

Vane J.R., et al., *Proc. Natl. Acad. Sci. USA*, 1994, 91, 2046.
U. S. Non–Provisional Application No. 09/798,752, filed Mar. 2, 2001 (our reference: PC10826A).
U.S. Non–Provisional Application No. 09/824,550, filed Apr. 2, 2001 (our reference: PC 10809A).
U.S. Provisional application No. 60 335, 736, filed Nov. 2, 2001 (our reference: PC23185).
U.S. Provisional application No. 60 335,738, filed Nov. 2, 2001 (our reference PC23166).
U.S. Provisional application No. 60/336,306, filed Nov. 2, 2001 (our reference: PC23181).
U.S. Provisional application No. 60/335,733, filed Nov. 2, 2001 (our reference: PC23182).
U.S. Provisional application No.60/335,713, filed Nov. 2, 2001 (our reference: PC23183).

*Primary Examiner*—Deborah C. Lambkin
*Assistant Examiner*—Sonya Wright
(74) *Attorney, Agent, or Firm*—Peter C. Richardson; Gregg C. Benson; Raymond D. Thompson

(57) ABSTRACT

An efficient synthesis of sulfonyl pyrazoles of formula I:

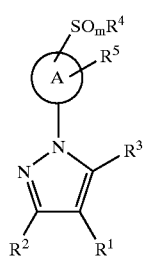

wherein the ring of the formula $(R^5)$-A-$(SO_mR^4)$, m, $R^1$ through $R^9$ are as defined in the specification, comprising reacting a compound of formula II:

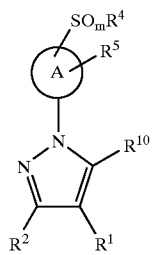

wherein the ring of the formula $(R^5)$-A-$(SO_mR^4)$, m $R^1$ through $R^9$ are as defined above and wherein $R^{10}$ is halo, $(C_1-C_6)$alkyl-$SO_3$—, $(C_6-C_{10})$aryl-$SO_3$—, $(C_1-C_6)$alkyl-$SO_2$—, or $(C_6-C_{10})$aryl-$SO_2$—; wherein each of said $(C_1-C_6)$alkyl component of said $(C_1-C_6)$alkyl-$SO_3$— and $(C_1-C_6)$alkyl-$SO_2$— radicals may optionally be substituted on any carbon atom by one to six fluoro substituents per $(C_1-C_6)$alkyl component; with a compound of formula $R^3$—H, wherein $R^3$ is as defined above, in the presence of a fluoride containing salt and in the presence of a solvent.

17 Claims, No Drawings

EFFICIENT SYNTHESIS OF 5-HETEROATOM-CONTAINING -PYRAZOLES

This application claims the benefit of U.S. provisional application 60/335,687, filed Nov. 2, 2001.

BACKGROUND OF THE INVENTION

The invention relates to the preparation of sulfonyl pyrazoles useful as anti-inflammatory/analgesic agents. It has now been found that the use of a metal fluoride salt allows processes of preparing sulfonyl pyrazoles containing versatile amino, ether, or thio ether component on the 5-position of the pyrazole ring to be performed at lower temperature, such as room temperature, with consistent higher yields.

The sulfonyl pyrazoles prepared by the methods of the present invention are useful in the treatment of cyclooxygenase (COX) mediated diseases, such as arthritis, neurodegeneration and colon cancer, in mammals, preferably humans, dogs, cats or livestock. Two forms of COX are now known, a constitutive isoform (COX-1) and an inducible isoform (COX-2) of which expression is upregulated at sites of inflammation (Vane, J. R.; Mitchell, et. al., *Proc. Natl. Acad. Sci. USA*, 1994, 91, 2046). COX-1 appears to play a physiological role and to be responsible for gastrointestinal and renal protection. On the other hand, COX-2 appears to play a pathological role and is believed to be the predominant isoform present in inflammation conditions. Preferred compounds prepared by the methods of the present invention are selective COX-2 inhibitors. Therapeutic use of conventional COX inhibitors is limited due to drug associated side effects, including life threatening ulceration and renal toxicity. Compounds that selectively inhibit COX-2 would exert anti-inflammatory effects without the adverse side effects associated with COX-1 inhibition.

A variety of sulfonylpyrazoles that inhibit COX have been prepared by other methods described in patent publications WO 97/11704, WO 01/40216, EP 1104758, EP 1104759, and EP 1104760; and U.S. Non-Provisional patent application Ser. No. 09/798,752, filed Mar. 2, 2001, and U.S. Non-Provisional patent application Ser. No. 09/824,550, filed Apr. 2, 2001. None of these methods use a fluoride containing salt.

Filed simultaneously with the present application on Nov. 2, 2001, are United States Provisional Applications entitled "Hydrazinyl and Nitrogen Oxide Pyrazoles"; "Heterocyclo-Alkylsulfonyl Pyrazoles"; "5-Heteroatom-Substituted Pyrazoles"; "5-Heterocyclo-pyrazoles"; and "5-(Alkylidene-Cycloalkyl)- and 5-(Alkylidene-Heterocyclyl)-Pyrazoles", which refer to certain pyrazole COX-2 inhibitors that can be prepared by the present processes of the invention. The aforesaid applications are herein incorporated in their entireties by reference.

SUMMARY OF THE INVENTION

The present invention relates to a process for preparing a compound of formula I:

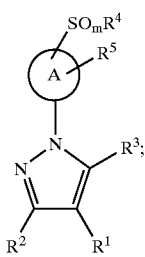

I or the pharmaceutically acceptable salts thereof; wherein the ring of the formula $(R^5)$-A-$(SO_mR^4)$ is selected from the group consisting of

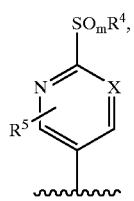

A1

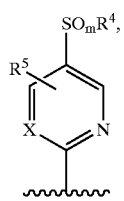

A2

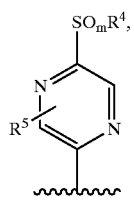

A3

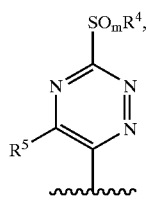

A4

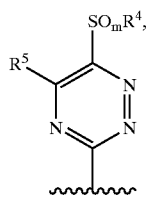

A5

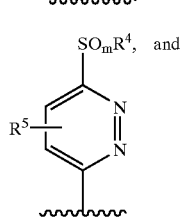

A6

-continued

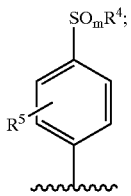
A7 m is 0, 1 or 2;

X is >CR$^5$ or >N;

R$^1$ is a radical selected from the group consisting of H, —NO$_2$, —CN, (C$_1$–C$_6$)alkyl, (C$_1$–C$_6$)alkyl-SO$_2$—, (C$_6$–C$_{10}$)aryl-SO$_2$—, H—(C=O)—, (C$_1$–C$_6$)alkyl-(C=O)—, (C$_1$–C$_6$)alkyl-O—(C=O)—, (C$_1$–C$_9$)heteroaryl-(C=O)—, (C$_1$–C$_9$)heterocyclyl-(C=O)—, H$_2$N—(C=O)—, (C$_1$–C$_6$)alkyl-NH—(C=O)—, [(C$_1$–C$_6$)alkyl]$_2$-N—(C=O)—, [(C$_6$–C$_{10}$)aryl]-NH—(C=O)—, [(C$_1$–C$_6$)alkyl]-[((C$_6$–C$_{10}$)aryl)-N]—(C=O)—, HO—NH—(C=O)—, and (C$_1$–C$_6$)alkyl-O—NH—(C=O)—;

R$^2$ is a radical selected from the group consisting of H, —NO$_2$, —CN, (C$_2$–C$_6$)alkenyl, (C$_2$–C$_6$)alkynyl, (C$_3$–C$_7$)cycloalkyl, (C$_6$–C$_{10}$)aryl, (C$_1$–C$_9$)heteroaryl, (C$_1$–C$_9$)heterocyclyl, (C$_1$–C$_6$)alkyl-O—, (C$_3$–C$_7$)cycloalkyl-O—, (C$_6$–C$_{10}$)aryl-O—, (C$_1$–C$_9$)heteroaryl-O—, (C$_1$–C$_9$)heterocyclyl-O—, H—(C=O)—, (C$_1$–C$_6$)alkyl-(C=O)—, (C$_3$–C$_7$)cycloalkyl-(C=O)—, (C$_6$–C$_{10}$)aryl-(C=O)—, (C$_1$–C$_9$)heteroaryl-(C=O)—, (C$_1$–C$_9$)heterocyclyl-(C=O)—, (C$_1$–C$_6$)alkyl-O—(C=O)—, (C$_3$–C$_7$)cycloalkyl-O—(C=O)—, (C$_6$–C$_{10}$)aryl-O—(C=O)—, (C$_1$–C$_9$)heteroaryl-O—(C=O)—, (C$_1$–C$_9$)heterocyclyl-O—(C=O)—, (C$_1$–C$_6$)alkyl-(C=O)—, (C$_3$–C$_7$)cycloalkyl-(C=O)—O—, (C$_6$–C$_{10}$)aryl-(C=O)—O—, (C$_1$–C$_9$)heteroaryl-(C=O)—O—, (C$_1$–C$_9$)heterocyclyl-(C=O)—O—, (C$_1$–C$_6$)alkyl-(C=O)—NH—, (C$_3$–C$_7$)cycloalkyl-(C=O)—NH—, (C$_6$–C$_{10}$)aryl-(C=O)—NH—, (C$_1$–C$_9$)heteroaryl-(C=O)—NH—, (C$_1$–C$_9$)heterocyclyl-(C=O)—NH—, (C$_1$–C$_6$)alkyl-O—(C=O)—NH—, (C$_1$–C$_6$)alkyl-NH, [(C$_1$–C$_6$)alkyl]$_2$-N—, (C$_3$–C$_7$)cycloalkyl-NH—, [(C$_3$–C$_7$)cycloalkyl]$_2$-N—, [(C$_6$–C$_{10}$)aryl]-NH—, [(C$_6$–C$_{10}$)aryl]$_2$-N—, [(C$_1$–C$_6$)alkyl]-[((C$_8$–C$_{10}$)aryl)-N]—, [(C$_1$–C$_9$)heteroaryl]-NH—, [(C$_1$–C$_9$)heteroaryl]$_2$-N—, [(C$_1$–C$_9$)heterocyclyl]-NH—, [(C$_1$–C$_9$)heterocyclyl]$_2$-N—, H$_2$N—(C=O)—, HO—NH—(C=O)—, (C$_1$–C$_6$)alkyl-O—NH—(C=)—, [(C$_1$–C$_6$)alkyl]-NH—(C=O)—, [(C$_1$–C$_6$)alkyl]$_2$-N—(C=O)—, [(C$_3$–C$_7$)cycloalkyl]-NH—(C=O)—, [(C$_3$–C$_7$)cycloalkyl]$_2$-N—(C=O)—, [(C$_6$–C$_{10}$)aryl]-NH—(C=O)—, [(C$_6$–C$_{10}$)aryl]$_2$-N—(C=O)—, [(C$_1$–C$_6$)alkyl]-[((C$_6$–C$_{10}$)aryl)-N]—(C=O)—, [(C$_1$–C$_9$)heteroaryl]-NH—(C=O)—, [(C$_1$–C$_9$)heteroaryl]$_2$-N—(C=O)—, [(C$_1$–C$_9$)heterocyclyl]-NH—(C=O)—, (C$_1$–C$_6$)alkyl-S— and (C$_1$–C$_6$)alkyl optionally substituted by one —OH group or by one to four fluoro substituents;

R$^3$ is a radical selected from the group consisting of

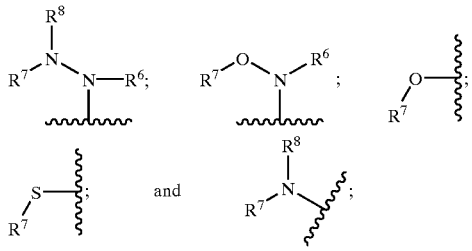

R$^6$ is a radical independently selected from the group consisting of H, (C$_1$–C$_6$)alkyl, (C$_2$–C$_6$)alkenyl, (C$_2$–C$_6$)alkynyl, H—(C=O)—, (C$_1$–C$_6$)alkyl-(C=O)—, (C$_1$–C$_6$)alkyl-O—(C=)—, H$_2$N—(C=O)—, [(C$_1$–C$_6$)alkyl]-NH—(C=O)—, [(C$_1$–C$_6$)alkyl]$_2$-N—(C=O)—, [(C$_8$–C$_{10}$)aryl]-NH—(C=O)—, [(C$_1$–C$_6$)alkyl]-[((C$_6$–C$_{10}$)aryl)-N]—(C=O)—, (C$_1$–C$_6$)alkyl-O—NH—(C=O)—, (C$_6$–C$_{10}$)aryl, (C$_3$–C$_8$)cycloalkyl, (C$_1$–C$_{10}$)heteroaryl and (C$_1$–C$_{10}$)heterocyclyl;

R$^7$ is a radical independently selected from the group consisting of (C$_1$–C$_6$)alkyl, (C$_2$–C$_6$)alkenyl, (C$_2$–C$_6$)alkynyl, H—(C=O)—, (C$_1$–C$_6$)alkyl-(C=O)—, (C$_1$–C$_6$)alkyl-O—(C=O)—, H$_2$N—(C=O)—, [(C$_1$–C$_6$)alkyl]-NH—(C=O)—, [(C$_1$–C$_6$)alkyl]$_2$-N—(C=O)—, [(C$_6$–C$_{10}$)aryl]-NH—(C=O)—, [(C$_1$–C$_6$)alkyl]-[((C$_6$–C$_{10}$)aryl)-N]—(C=O)—, (C$_1$–C$_6$)alkyl-O—NH—(C=O)—, (C$_6$–C$_{10}$)aryl, (C$_3$–C$_8$)cycloalkyl, (C$_1$–C$_{10}$)heteroaryl and (C$_1$–C$_{10}$)heterocyclyl; or R$^6$ and R$^7$ may optionally be taken together with the nitrogen or the oxygen to which they are attached to form a 3- to 8-membered heterocyclic ring radical; wherein said 3- to 8-membered heterocyclic ring radical may optionally contain at least one nitrogen or one oxygen heteroatom in addition to said nitrogen or said oxygen to which R$^6$ and R$^7$ are attached;

wherein said 3- to 8-membered heterocyclic ring radical made up of R$^6$ and R$^7$ may optionally be substituted on any ring carbon atom by one to three substituents per ring independently selected from the group consisting of halo, —OH, (C$_1$–C$_6$)alkyl-O—, and (C$_1$–C$_6$)alkyl optionally substituted by one to four fluoro moieties;

wherein said 3- to 8-membered heterocyclic ring radical made up of R$^6$ and R$^7$ may optionally be substituted on any ring carbon atom by at least one oxo or one (C$_1$–C$_6$)alkylidene substituent per ring;

R$^8$ is a radical selected from the group consisting of H, (C$_1$–C$_6$)alkyl, (C$_2$–C$_6$)alkenyl, (C$_2$–C$_6$)alkynyl, H—(C=O)—, (C$_1$–C$_6$)alkyl-(C=O)—, (C$_1$–C$_6$)alkyl-O—(C=O)—, H$_2$N—(C=O)—, [(C$_1$–C$_6$)alkyl]-NH—(C=O)—, [(C$_1$–C$_6$)alkyl]$_2$-N—(C=O)—, [(C$_6$–C$_{10}$)aryl]-NH—(C=O)—, [(C$_1$–C$_6$)alkyl]-[((C$_6$–C$_{10}$)aryl)-N]—(C=O)—, (C$_1$–C$_6$)alkyl-O—NH—(C=O)—, (C$_6$–C$_{10}$)aryl, (C$_3$–C$_8$)cycloalkyl, (C$_1$–C$_{10}$)heteroaryl and (C$_1$–C$_{10}$)heterocyclyl; or R$^7$ and R$^8$ may optionally be taken together with the nitrogen to which they are attached to form a 3- to 8-membered heterocyclic ring radical; wherein said 3- to 8-membered heterocyclic ring radical may optionally contain at least one nitrogen or one oxygen heteroatom in addition to said nitrogen to which R$^7$ and R$^8$ are attached;

wherein said 3- to 8-membered heterocyclic ring radical made up of $R^7$ and $R^8$ may optionally be substituted on any ring carbon atom by one to three substituents per ring independently selected from the group consisting of halo, —OH, $(C_1–C_6)$alkyl-O— and $(C_1–C_6)$alkyl optionally substituted by one to four fluoro moieties;

wherein said 3- to 8-membered heterocyclic ring radical made up of $R^7$ and $R^8$ may optionally be substituted on any ring carbon atom by at least one oxo or one $(C_1–C_6)$alkylidene substituent per ring;

wherein each of $R^6$, $R^7$, or $R^8$ $(C_1–C_6)$alkyl radicals may optionally be substituted on any carbon atom by one to three substituents per $(C_1–C_6)$alkyl components independently selected from the group consisting of halo, —OH, $(C_1–C_6)$alkyl-O—, $(C_2–C_6)$alkenyl, $(C_2–C_6)$alkynyl, $(C_3–C_7)$cycloalkyl, $(C_6–C_{10})$aryl, $(C_1–C_9)$heteroaryl, $(C_1–C_{10})$heterocyclyl, —CN, H—(C=O)—, $(C_1–C_6)$alkyl-(C=O)—, $(C_1–C_6)$alkyl-(C=O)—O—, HO—(C=O)—, $(C_1–C_6)$alkyl-O—(C=O)—, $(C_1–C_6)$alkyl-NH—, [$(C_1–C_6)$alkyl]$_2$-N—, $(C_3–C_7)$cycloalkyl-NH—, $(C_6–C_{10})$aryl-NH—, [$(C_1–C_6)$alkyl]-[$((C_6–C_{10})$aryl)-N]—, $(C_1–C_9)$heteroaryl-NH—, $(C_1–C_{10})$heterocyclyl-NH—, $H_2N$—(C=O)—, [$(C_1–C_6)$alkyl]-NH—(C=O)—, [$(C_1–C_6)$alkyl]$_2$-N—(C=O)—, [$(C_6–C_{10})$aryl]-NH—(C=O)—, [$(C_1–C_6)$alkyl]-[$((C_6–C_{10})$aryl)-N]—(C=O)—, $(C_1–C_6)$alkyl-O—NH—(C=O)—, and $(C_1–C_6)$alkyl-S—;

wherein each of $R^6$, $R^7$, or $R^8$ $(C_6–C_{10})$aryl, $(C_3–C_8)$cycloalkyl, $(C_1–C_{10})$heteroaryl and $(C_1–C_{10})$heterocyclyl ring radicals may optionally be substituted on any ring carbon atom by one to three substituents per ring independently selected from the group consisting of halo, —OH, $(C_1–C_6)$alkyl-O—, $(C_2–C_6)$alkenyl, $(C_2–C_6)$alkynyl, $(C_3–C_7)$cycloalkyl, —CN, H—(C=O)—, $(C_1–C_6)$alkyl-(C=O)—, $(C_1–C_6)$alkyl-(C=O)—O—, HO—(C=O)—, $(C_1–C_6)$alkyl-O—(C=O)—, $(C_1–C_6)$alkyl-NH—, [$(C_1–C_6)$alkyl]$_2$-N—, $(C_3–C_7)$cycloalkyl-NH—, $(C_6–C_{10})$aryl-NH—, [$(C_1–C_6)$alkyl]-[$(C_6–C_{10})$aryl]-N—, $(C_1–C_9)$heteroaryl-NH—, $H_2N$—(C=O)—, [$(C_1–C_6)$alkyl]-NH—(C=O)—, [$(C_1–C_6)$alkyl]$_2$-N—(C=O)—, [$(C_6–C_{10})$aryl]-NH—(C=O)—, [$(C_1–C_6)$alkyl]-[$(C_6–C_{10})$aryl]-N—(C=O)—, $(C_1–C_6)$alkyl-O—NH—(C=O)—, $(C_1–C_6)$alkyl-S—, and $(C_1–C_6)$alkyl optionally substituted by one to four fluoro moieties;

wherein each of $R^6$, $R^7$, or $R^8$ $(C_3–C_8)$cycloalkyl and $(C_1–C_{10})$heterocyclyl radicals or substituents, respectively, may also optionally be substituted on any ring carbon atom by at least one oxo or one $(C_1–C_6)$alkylidene substituent or moiety, respectively, per ring;

$R^4$ is a radical selected from the group consisting of —NH$_2$, $(C_1–C_6)$alkyl-NH—, [$(C_1–C_6)$alkyl]$_2$-N—, $(C_1–C_6)$alkyl-(C=O)—NH—, $(C_6–C_{10})$aryl-(C=O)—NH—, [$(C_6–C_{10})$aryl$(C_1–C_6)$alkyl]-(C=O)—NH—, $(C_1–C_6)$alkyl-O—(C=O)—NH—, $(C_6–C_{10})$aryl-O—(C=O)—NH—, [$(C_1–C_6)$alkyl]-NH—(C=O)—NH—, [$(C_1–C_6)$alkyl]$_2$-N—(C=O)—NH—, [$(C_6–C_{10})$aryl]-NH—(C=O)—NH—, [$(C_1–C_6)$alkyl]-NH—HC=N—, [$C_1–C_6)$alkyl]$_2$N—HC=N—, or [$(C_6–C_{10})$aryl]-NH—HC=N—, and and $(C_1–C_6)$alkyl optionally substituted by one to four —OH substituents; and $R^5$ is a radical selected from the group consisting of H, halo, —OH, $(C_1–C_6)$alkyl-O—, $(C_2–C_6)$alkenyl, $(C_2–C_6)$alkynyl, $(C_3–C_7)$cycloalkyl, —CN, H—(C=O)—, $(C_1–C_6)$alkyl-(C=O)—, $(C_1–C_6)$alkyl-(C=O)—O—, HO—(C=O)—, $(C_1–C_6)$alkyl-O—(C=O)—, $(C_1–C_6)$alkyl-NH—, [$(C_1–C_6)$alkyl]$_2$-N—, $(C_3–C_7)$cycloalkyl-NH—, $(C_6–C_{10})$aryl-NH—, [$(C_1–C_6)$alkyl]-[$((C_6–C_{10})$aryl)-N]—, $(C_1–C_9)$heteroaryl-NH—, $H_2N$—(C=O)—, $(C_1–C_6)$alkyl-NH—(C=O)—, [$(C_1–C_6)$alkyl]$_2$-N—(C=O)—, $(C_6–C_{10})$aryl-(C=O)—, [$(C_1–C_6)$alkyl]-[$((C_6–C_{10})$aryl)-N]—(C=O)—, $(C_1–C_6)$alkyl-O—NH—(C=O)—, $(C_1–C_6)$alkyl-S—, and, $(C_1–C_6)$alkyl optionally substituted by one to four fluoro substituents;

comprising reacting a compound of the formula II:

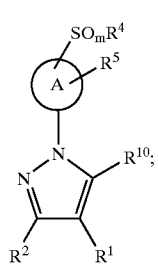

II wherein the ring of the formula $(R^5)$-A-$(SO_mR^4)$, m, and $R^1$ through $R^5$ are as defined above, and wherein $R^{10}$ is a radical selected from the group consisting of halo, $(C_1–C_6)$alkyl-SO$_3$—, $(C_6–C_{10})$aryl-SO$_3$—, $(C_1–C_6)$alkyl-SO$_2$—, and $(C_6–C_{10})$aryl-SO$_2$—, wherein each of said $(C_1–C_6)$alkyl component of said $(C_1–C_6)$alkyl-SO$_3$— and $(C_1–C_6)$alkyl-SO$_2$— radicals is optionally substituted by one to six fluoro substituents;

with a compound of formula $R^3$—H, wherein $R^3$ is as defined above, in the presence of a fluoride containing salt; in the presence of a solvent.

The compounds prepared by the process of this invention include all stereoisomers (e.g., cis and trans isomers) and all optical isomers of compounds of the formula I (e.g., R and S enantiomers), as well as racemic, diastereomeric and other mixtures of such isomers.

The compounds prepared by the process of this invention may also exist in different tautomeric forms. This invention relates to process to prepare all tautomers of formula I.

The compounds prepared by the process of this invention may contain olefin-like double bonds. When such bonds are present, the process of the invention prepares all compounds of formula I in cis and trans configurations and in mixtures thereof.

Unless otherwise indicated, the term "functional group" refers to "radical", "substituent" "moiety", or "sub-moiety", as defined below. The term "sub-functional group" refers to "substituent" "moiety", or "sub-moiety", as defined below.

Unless otherwise indicated, the term "radical" or "radicals" refers to an individual member of a variable ($R^1$, $R^2$, $R^3$ etc) of the compound of the formula I (e.g., $R^1$ is a radical selected from the group consisting of H and $(C_1–C_6)$alkyl means that $R^1$ can be either a H radical or a $(C_1–C_6)$alkyl radical).

Unless otherwise indicated, the term "substituent" or "substituents" refers to a replacement of at least one atom of a radical, wherein the term "radical" is as defined above, by another atom or group of atoms. For example, an $(C_1–C_6)$alkyl substituent may replace a hydrogen atom of $R^1$ $(C_6–C_{10})$aryl radical.

Unless otherwise indicated, the term "moiety" or "moieties" refers to a replacement of at least one atom of a substituent, wherein the term "substituent" is as defined above, by another atom or group of atoms. For example, an ($C_1$–$C_6$)alkyl moiety of a particular substituent (e.g., ($C_1$–$C_6$)alkyl, ($C_6$–$C_{10}$)aryl, or ($C_3$–$C_8$)cycloalkyl substituent) may replace a hydrogen atom of that substituent.

Unless otherwise indicated, the term "sub-moiety" or "sub-moieties" refers to a replacement of at least one atom of a moiety, wherein the term "moiety" is as defined above, by another atom or group of atoms. For example, an ($C_1$–$C_6$) alkyl sub-moiety of a particular moiety (e.g., ($C_1$–$C_6$)alkyl, ($C_6$–$C_{10}$)aryl, or ($C_3$–$C_8$)cycloalkyl moiety) may replace a hydrogen atom of that moiety.

Unless otherwise indicated, the term "($C_1$–$C_6$)alkyl" as well as the ($C_1$–$C_6$)alkyl component of other terms referred to herein (e.g., the "($C_1$–$C_6$)alkyl component of ($C_1$–$C_6$) alkyl-O—), may be linear or branched (such as methyl, ethyl, n-propyl, isopropyl, n-butyl, iso-butyl, secondary-butyl, tertiary-butyl), wherein each of said ($C_1$–$C_6$)alkyl functional group, wherever they occur, may optionally be substituted by one to three sub-functional groups per ($C_1$–$C_6$)alkyl component independently selected from the group consisting of fluoro, —OH, ($C_2$–$C_6$)alkenyl, ($C_2$–$C_6$) alkynyl, ($C_3$–$C_7$)cycloalkyl, ($C_1$–$C_6$)alkyl-O—, oxo, H—(C=O)—, $H_2$N—(C=O)—, ($C_1$–$C_6$)alkyl-(C=O)—, —CN, —$NO_2$, ($C_1$–$C_6$)alkyl-O—(C=O)—, ($C_1$–$C_6$)alkyl-NH—, [($C_1$–$C_6$)alkyl]$_2$-N—, ($C_3$–$C_7$)cycloalkyl-NH—, ($C_6$–$C_{10}$)aryl-NH—, [($C_1$–$C_6$)alkyl]-[(($C_6$–$C_{10}$)aryl)-N]—, ($C_1$–$C_9$)heteroaryl-NH—, ($C_1$–$C_{10}$)heterocyclyl-NH—, $H_2$N—(C=O)—, [($C_1$–$C_6$)alkyl]-NH—(C=O)—, [($C_1$–$C_6$)alkyl]$_2$-N—(C=O)—, [($C_6$–$C_{10}$)aryl]-NH—(C=O)—, [($C_1$–$C_6$)alkyl]-[(($C_6$–$C_{10}$)aryl)-N]—(C=O)—, ($C_1$–$C_6$)alkyl-O—NH—(C=O)—, ($C_6$–$C_{10}$)aryl, ($C_2$–$C_9$) heteroaryl, ($C_6$–$C_{10}$)aryl-O—, ($C_1$–$C_9$)heteroaryl-O—, ($C_1$–$C_9$)heteroaryl-(C=O)—, ($C_1$–$C_6$)alkyl-S—, ($C_1$–$C_6$) alkyl-S(=O)—, ($C_1$–$C_6$)alkyl-$SO_2$—, ($C_1$–$C_6$)alkyl-(C=O)—NH—, ($C_1$–$C_6$)alkyl-(C=O)—NH—($C_1$–$C_6$) alkyl-NH and ($C_1$–$C_6$)alkyl-(C=O)—O—.

Unless otherwise indicated, the term "($C_1$–$C_6$)alkyl radicals may optionally be substituted on any carbon atom by one to three substituents per ($C_1$–$C_6$)alkyl components" refers to a replacement of at least one atom of any ($C_1$–$C_6$) alkyl components of any radicals containing an ($C_1$–$C_6$) alkyl component, wherein the term "radical" is as defined above, by another atom or group of atoms. Radicals containing an ($C_1$–$C_6$)alkyl component include, but are not limited to, ($C_1$–$C_6$)alkyl-(C=O)—, ($C_1$–$C_6$)alkyl-(C=O)—O—, ($C_1$–$C_6$)alkyl-O—(C=O)—, ($C_1$–$C_6$)alkyl-NH—, [($C_1$–$C_6$)alkyl]$_2$-N—, [($C_1$–$C_6$)alkyl]-[(($C_6$–$C_{10}$) alkyl-NH—(C=O)—, [($C_1$–$C_6$)alkyl]$_2$-N—(C=O)—, [($C_1$–$C_6$)alkyl]-[(($C_6$–$C_{10}$)aryl)-N]—(C=O)—, ($C_1$–$C_6$) alkyl-O—NH—(C=O)—, and ($C_1$–$C_6$)alkyl-S—.

Unless otherwise indicated, the term "halo" means fluoro, chloro, bromo or iodo.

Unless otherwise indicated, the term "($C_2$–$C_6$)alkenyl" means straight or branched hydrocarbon chain functional groups of 2 to 6 carbon atoms having at least one double bond including, but not limited to ethenyl, 1-propenyl, 2-propenyl (allyl), iso-propenyl, 2-methyl-1-propenyl, 1-butenyl, or 2-butenyl.

Unless otherwise indicated, the term "($C_1$–$C_6$)alkylidene" refers to functional groups of the formula =$CH_2$ or =($CH_m$)$_n$$CH_3$, wherein m is 0 to 2 and n is 1 to 5, such as methylidine (=$CH_2$), ethylidine (=CH—$CH_3$), propylidene (=CH—$CH_2CH_3$), or butylidene (=CH—$CH_2CH_2CH_3$). Said ($C_1$–$C_6$)alkylidene functional groups may be branched such as 1-methyl-ethylidine (=C($CH_3$)—$CH_3$).

Unless otherwise indicated, the term "($C_2$–$C_6$)alkynyl" is used herein to mean straight or branched hydrocarbon chain functional groups of 2 to 6 carbon atoms having one triple bond including, but not limited to, ethynyl (—C≡C—H), propynyl (—$CH_2$—C≡C—H or —C≡C—$CH_3$), or butynyl (—$CH_2$—$CH_2$—C≡C—H, or —$CH_2$—C≡C—$CH_3$, or —C≡C—$CH_2CH_3$).

Unless otherwise indicated, the term "($C_3$–$C_7$)cycloalkyl" refers to a mono or bicyclic carbocyclic ring functional groups including, but not limited to, cyclopropyl, cyclobutyl, cyclopentyl, cyclohexyl, cycloheptyl, cyclooctyl, cyclononyl, bicyclo[2.2.1]heptanyl, bicyclo[3.2.1]octanyl and bicyclo[5.2.0]nonanyl; wherein said ($C_3$–$C_7$)cycloalkyl functional groups may optionally contain 1 or 2 double bonds including, but not limited to, cyclopentenyl, cyclohexenyl, and cycloheptenyl.

Unless otherwise indicated, the term "($C_6$–$C_{10}$)aryl" means aromatic functional groups such as phenyl, naphthyl, tetrahydronaphthyl, or indanyl, wherein said ($C_6$–$C_{10}$)aryl functional groups are optionally substituted on any ring carbon atom by one to two sub-functional groups per ring, wherein said substituents are independently selected from the group consisting of halo, —OH, —CN, —SH, HO—(C=O)—, —$NO_2$, ($C_1$–$C_6$)alkyl, ($C_2$–$C_6$)alkenyl, ($C_2$–$C_6$) alkynyl, ($C_3$–$C_7$)cycloalkyl, ($C_6$–$C_{10}$)aryl, ($C_1$–$C_9$) heteroaryl, ($C_1$–$C_9$($C_1$–$C_6$)alkyl-O—, —$OCF_3$, ($C_1$–$C_6$) alkyl-S—, ($C_1$–$C_6$)alkyl-NH—, [($C_1$–$C_6$)alkyl]$_2$-N—, ($C_3$–$C_7$)cycloalkyl-NH—, ($C_6$–$C_{10}$)aryl-NH—, [($C_1$–$C_6$) alkyl]-[(($C_6$–$C_{10}$)aryl)-N]—, ($C_1$–$C_9$)heteroaryl-N—, ($C_1$–$C_{10}$)heterocyclyl-NH—, $H_2$N—(C=O)—, [($C_1$–$C_6$) alkyl]-NH—(C=O)—, [($C_1$–$C_6$)alkyl]$_2$-N—(C=O)—, [($C_6$–$C_{10}$)aryl]-NH—(C=O)—, [($C_1$–$C_6$)alkyl]-[(($C_6$–$C_{10}$) aryl)-N]—(C=O)—, ($C_1$–$C_6$)alkyl-O—NH—(C=O)—, ($C_1$–$C_6$)alkyl-(C=O)—O—, ($C_1$–$C_6$)alkyl-(C=O)—NH—($C_1$–$C_6$)alkyl-(C=O)—HN—($C_1$–$C_6$)alkyl-NH, H—(C=O)—, ($C_1$–$C_6$)alkyl-(C=O)—, and ($C_1$–$C_6$)alkyl-O—(C=O)—.

Unless otherwise indicated, the term "[($C_1$–$C_6$)alkyl]-[(($C_6$–$C_{10}$)aryl)-N]—" has the following structure:

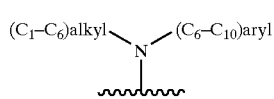

wherein the term "($C_1$–$C_6$)alkyl" and the term "($C_6$–$C_{10}$) aryl" are as defined above.

Unless otherwise indicated, the term "[($C_1$–$C_6$)alkyl]-[(($C_6$–$C_{10}$)aryl)-N]—(C=O)—" has the following structure:

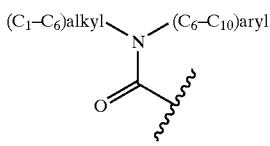

wherein the term "$(C_1-C_6)$" and the term "$(C_6-C_{10})$" are as defined above.

Unless otherwise indicated, the term "$(C_1-C_6)$alkyl-$(C=O)$—HN—$(C_1-C_6)$alkyl-NH" has the following structure:

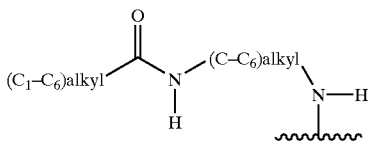

wherein the term "$(C_1-C_6)$alkyl" is as defined above.

Unless otherwise indicated, the term "oxo" refers to =O.

Unless otherwise indicated, the term "$[(C_1-C_6)$alkyl]-NH—HC=N—" refers to

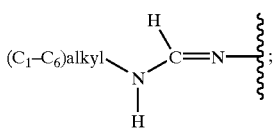

wherein the term "$(C_1-C_6)$alkyl" is as defined above

Unless otherwise indicated, the term "$C_1-C_6)$alkyl]$_2$N—HC=N—" refers to

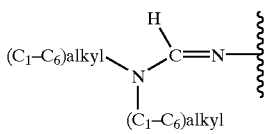

wherein the term "$(C_1-C_6)$alkyl" is as defined above

Unless otherwise indicated, the term "$[(C_6-C_{10})$alkyl]-NH—HC=N—" refers to

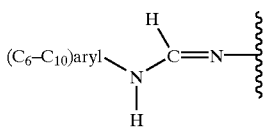

wherein the term "$(C_6-C_{10})$aryl" is as defined above.

Unless otherwise indicated, the term "$(C_1-C_9)$heteroaryl" refers to aromatic or multicyclic ring functional groups wherein at least one ring functional groups is aromatic, wherein said aromatic or multicyclic ring functional groups contain one or more heteroatoms selected from the group consisting of O, S, and N. The $(C_1-C_9)$heteroaryl functional groups can also be optionally substituted by one or more oxo sub-functional groups. Examples of heteroaryl functional groups include, but not limited to, benzimidazoylyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl functional group is optionally substituted on any atoms capable of forming an additional bond by one or two sub-functional groups independently selected from halo, —CN, —OH, $(C_1-C_6)$alkyl, perfluoro$(C_1-C_6)$alkyl, perfluoro$(C_1-C_6)$alkyl-O— and $(C_3C_8)$cycloalkyl-O—. The foregoing $(C_1-C_9)$heteroaryls functional groups can be C-attached or N-attached where such is possible. For instance, pyrrolyl can be pyrrol-1-yl (N-attached) or pyrrol-3-yl (C-attached).

Unless otherwise indicated, the term "$(C_1-C_9)$ heterocyclyl" refers to a cyclic functional group containing 1 to 9 carbon atoms and 1 to 4 heteroatoms selected from the group consisting of N, O, and S. The heterocyclyl ring functional groups can be optionally substituted where such is possible by oxo, —CN, —OH, $(C_1-C_6)$alkyl, perfluoro $(C_1-C_6)$alkyl, perfluoro$(C_1-C_6)$alkyl-O—, $(C_1-C_6)$alkyl-O— and $(C_3-C_8)$cycloalkyl-O—. Examples of the cyclic functional groups include, but not limited to, 3-azabicyclo [3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. The foregoing heterocyclyl can be C-attached or N-attached where such is possible. For example, piperidinyl can be piperidin-1-yl (N-attached) or piperidin-4-yl (C-attached).

In a preferred embodiment of the process of the invention, said fluoride containing salt contains a cationic metal selected from the group consisting of lithium, sodium, potassium, cesium, magnesium, calcium, strontium, and barium, more preferably potassium or cesium.

In another preferred embodiment of the process of the invention, wherein said fluoride containing salt contains a cationic metal as defined above, 0.01 to 15 equivalents, preferably 1 to 10 equivalents, of said fluoride containing salt relative to the compound of the formula I is used.

Unless otherwise indicated, the term "equivalents" refers to the number of moles of the fluoride containing salt relative to the number of moles of the compound of the formula I.

In another preferred embodiment of the process of the invention, wherein said fluoride containing salt contains a cationic metal as defined above, said process is performed at a temperature of about 5° C. to about 40° C., preferably about 10° C. to about 30° C.

In another preferred embodiment of the process of the invention, wherein said fluoride containing salt contains a cationic metal as defined above, said process is performed in the presence of a solvent selected from the group consisting of dimethylsulfoxide, dimethylformamide, dimethylacetamide, acetone and acetonitrile.

In another preferred embodiment of the process of the invention, said fluoride containing salt is tetra($C_1$–$C_8$) alkylammonium fluoride or ($C_1$–$C_{16}$)alkyltri($C_1$–$C_2$) alkylammonium fluoride; more preferably tetrabutylammonium fluoride or cetyltrimethylammonium fluoride.

In another preferred embodiment of the process of the invention, wherein said fluoride containing salt is tetra ($C_1$–$C_8$)alkylammonium fluoride or ($C_1$–$C_{16}$)alkyltri ($C_1$–$C_2$)alkylammonium fluoride; about 0.05 to about 5 equivalents; preferably 0.1 to 2 equivalents, of said fluoride containing salt relative to the compound of the formula I is used.

In another preferred embodiment of the process of the invention, wherein said fluoride containing salt is tetra ($C_1$–$C_8$)alkylammonium fluoride or ($C_1$–$C_{16}$)alkyltri ($C_1$–$C_2$)alkylammonium fluoride; said process is performed at a temperature of about 10° C. to about 100° C.; preferably about 20° C. to about 80° C.

In another preferred embodiment of the process of the invention, wherein said fluoride containing salt is tetra ($C_1$–$C_8$)alkylammonium fluoride or ($C_1$–$C_{16}$)alkyltri ($C_1$–$C_2$)alkylammonium fluoride; said process is performed in the presence of a solvent selected from the group consisting of acetonitrile, dichloromethane, chloroform, tetrahydrofuran and dichloroethane; more preferably tetrahydrofuran.

In another embodiment of the process of the invention, $R^{10}$ is a radical selected from the group consisting of halo, ($C_1$–$C_6$)alkyl-$SO_3$—, ($C_6$–$C_{10}$)aryl-$SO_3$—, ($C_1$–$C_6$)alkyl-$SO_2$—, or ($C_6$–$C_{10}$)aryl-$SO_2$—, wherein said ($C_1$–$C_6$)alkyl component of said ($C_1$–$C_6$)alkyl-$SO_3$—($C_1$–$C_6$)alkyl-$SO_2$— radicals is optionally substituted by one to six fluoro substituents; more preferably $R^{10}$ is a radical selected from the group consisting of chloro, bromo, methyl-$SO_3$—, phenyl-$SO_3$—, methyl-$SO_2$—, and phenyl-$SO_3$—; most preferably $R^{10}$ is chloro.

In another preferred embodiment of the process of the invention, $R^{10}$ is $CF_3$-$SO_3$—or $CF_3CF_2$—$SO_3$—.

In another embodiment of the process of the invention, in said compound of formula $R^3$—H, $R^3$ is a radical selected from the group consisting of

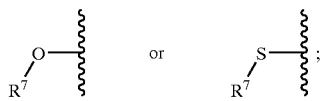

wherein $R^7$ is preferably a radical selected from the group consisting of ($C_1$–$C_6$)alkyl, ($C_6$–$C_{10}$)aryl, ($C_3$–$C_8$) cycloalkyl, ($C_1$–$C_{10}$)heteroaryl and ($C_1$–$C_{10}$) heterocyclyl; more preferably a radical selected from the group consisting of ($C_1$–$C_6$)alkyl, ($C_3$–$C_8$) cycloalkyl, and ($C_1$–$C_{10}$)heterocyclyl; most preferably a radical selected from the group consisting of methyl, tert-butyl, cyclohexyl, cyclopentyl piperidinyl, and morpholinyl;

wherein each $R^7$ ($C_1$–$C_6$)alkyl radicals may optionally be substituted on any carbon atom by one to three substituents per ($C_1$–$C_6$)alkyl components independently selected from the group consisting of ($C_3$–$C_7$) cycloalkyl, ($C_6$–$C_{10}$)aryl, ($C_1$–$C_9$)heteroaryl, and ($C_1$–$C_{10}$)heterocyclyl; preferably ($C_3$–$C_7$)cycloalkyl; more preferably cyclohexyl or cyclopentyl.

wherein each $R^7$ ($C_6$–$C_{10}$)aryl, ($C_3$–$C_8$)cycloalkyl, ($C_1$–$C_{10}$)heteroaryl and ($C_1$–$C_{10}$)heterocyclyl ring radicals may optionally be substituted on any ring carbon atom by one to three substituents per ring independently selected from the group consisting of halo and ($C_1$–$C_6$)alkyl optionally substituted by one to four fluoro moieties;

wherein each of $R^7$ ($C_3$–$C_8$)cycloalkyl and ($C_1$–$C_{10}$) heterocyclyl radicals may also optionally be substituted on any ring carbon atom by at least one ($C_1$–$C_6$) alkylidene substituent per ring.

In another embodiment of the process of the invention, in said compound of formula $R^3$—H, $R^3$ is

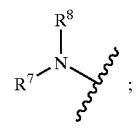

wherein $R^7$ is a radical selected from the group consisting of ($C_1$–$C_6$)alkyl, ($C_6$–$C_{10}$)aryl, ($C_3$–$C_8$)cycloalkyl, ($C_1$–$C_{10}$)heteroaryl and ($C_1$–$C_{10}$)heterocyclyl; preferably a radical selected from the group consisting of ($C_1$–$C_6$)alkyl, ($C_3$–$C_8$)cycloalkyl, and ($C_1$–$C_{10}$) heterocyclyl; more preferably a radical selected from the group consisting of methyl, tert-butyl, cyclohexyl, cyclopentyl, piperidinyl, and morpholinyl; and $R^8$ is a radical selected from the group consisting of H and ($C_1$–$C_6$)alkyl; preferably H;

wherein each of $R^7$ or $R^8$ ($C_1$–$C_6$)alkyl radicals may optionally be substituted on any carbon atom by one to three substituents per ($C_1$–$C_6$)alkyl radicals independently selected from the group consisting of halo and —OH;

wherein each of $R^7$ ($C_6$–$C_{10}$)aryl, ($C_3$–$C_8$)cycloalkyl, ($C_1$–$C_{10}$)heteroaryl and ($C_1$–$C_{10}$)heterocyclyl ring radicals may optionally be substituted on any ring carbon atom by one to three ($C_1$–$C_6$)alkyl substituents per ring wherein each of said ($C_1$–$C_6$)alkyl substituents are optionally substituted by one to four fluoro moieties;

wherein each of $R^7$ ($C_3$–$C_8$)cycloalkyl and ($C_1$–$C_{10}$) heterocyclyl radicals may also optionally be substituted on any ring carbon atom by at least one oxo or one ($C_1$–$C_6$)alkylidene substituent per ring.

In another embodiment of the process of the invention, in said compound of formula $R^3$—H, $R^3$ is

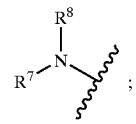

wherein $R^7$ and $R^8$ are taken together with the nitrogen to which they are attached to form a 3- to 8-membered heterocyclic ring radical; preferably a 5- to 6-membered heterocyclic ring radical; more preferably piperidinyl and morpholinyl;

wherein said 3- to 8-membered heterocyclic ring radical may optionally contain at least one nitrogen or one oxygen heteroatom in addition to said nitrogen to which $R^7$ and $R^8$ are attached;

wherein said 3- to 8-membered heterocyclic ring radical made up of $R^7$ and $R^8$ may optionally be substituted on any ring carbon atom by one to three $(C_1-C_6)$alkyl; preferably methyl; substituents per ring.;

wherein said 3- to 8-membered heterocyclic ring radical made up of $R^7$ and $R^8$ may optionally be substituted on any ring carbon atom by at least one $(C_1-C_6)$alkylidene substituent per ring.

In another embodiment of the process of the invention, in said compound of formula $R^3$—H, $R^3$ is

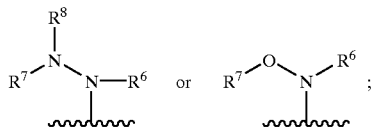

wherein $R^6$ is preferably H or $(C_1-C_6)$alkyl;

$R^7$ is a radical independently selected from the group consisting of $(C_1-C_6)$alkyl, $(C_6-C_{10})$aryl, $(C_3-C_8)$cycloalkyl, $(C_1-C_{10})$heteroaryl and $(C_1-C_{10})$heterocyclyl; preferably a radical independently selected from the group consisting of $(C_1-C_6)$alkyl, $(C_6-C_{10})$aryl, $(C_1-C_{10})$heteroaryl and $(C_1-C_{10})$heterocyclyl; more preferably a radical independently selected from the group consisting of methyl, ethyl, isobutyl, tert-butyl, phenyl, tetrahydrofuranyl, piperazinyl, morpholinyl, azepanyl, piperidinyl, and triazolyl;

$R^8$ is a radical independently selected from the group consisting of H, $(C_1-C_6)$alkyl, $(C_2-C_6)$alkenyl, $(C_2-C_6)$alkynyl, $(C_6-C_{10})$aryl, $(C_3-C_8)$cycloalkyl, $(C_1-C_{10})$heteroaryl and $(C_1-C_{10})$heterocyclyl; preferably a radical independently selected from the group consisting of H and $(C_1-C_6)$alkyl;

wherein each of $R^6$, $R^7$, or $R^8$ $(C_1-C_6)$alkyl radicals may optionally be substituted on any carbon atom by one to three substituents per $(C_1-C_6)$alkyl radicals independently selected from the group consisting of halo, —OH, and $(C_1-C_6)$alkyl-O—; preferably halo and methyl-O;

wherein each of $R^7$ or $R^8$ $(C_6-C_{10})$aryl, $(C_3-C_8)$cycloalkyl, $(C_1-C_{10})$heteroaryl and $(C_1-C_{10})$heterocyclyl ring radicals may optionally be substituted on any ring carbon atom by one to three substituents per ring independently selected from the group consisting of halo, —OH and $(C_1-C_6)$alkyl optionally substituted by one to four fluoro moieties; preferably by one to three substituents per ring independently selected from the group consisting of chloro, bromo and methyl;

wherein each of $R^7$ or $R^8$ $(C_3-C_8)$cycloalkyl and $(C_1-C_{10})$heterocyclyl radicals may also optionally be substituted on any ring carbon atom by at least one methylidene substituent per ring.

In an embodiment of the process of the invention, in said compound of formula $R^3$—H, $R^3$ is

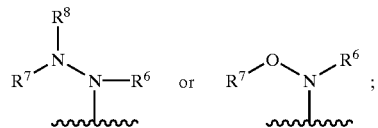

wherein $R^6$ and $R^7$ are taken together with the nitrogen or the oxygen to which they are attached to form a 3- to 8-membered heterocyclic ring radical; preferably a 5- to 6-membered heterocyclic ring radical; more preferably pyrazolidin-1-yl;

wherein said 3- to 8-membered heterocyclic ring radical may optionally contain at least one nitrogen or one oxygen heteroatom in addition to said nitrogen or said oxygen to which $R^6$ and $R^7$ are attached;

wherein said 3- to 8-membered heterocyclic ring radical made up of $R^6$ and $R^7$ may optionally be substituted on any ring carbon atom by one to three substituents per ring independently selected from the group consisting of halo, —OH, $(C_1-C_6)$alkyl-O—, and $(C_1-C_6)$alkyl optionally substituted by one to four fluoro moieties;

wherein said 3- to 8-membered heterocyclic ring radical made up of $R^6$ and $R^7$ may optionally be substituted on any ring carbon atom by at least one oxo or one $(C_1-C_6)$alkylidene substituent per ring; more preferably one oxo substituent per ring.

In an embodiment of the process of the invention, in said compound of formula $R^3$—H, $R^3$ is

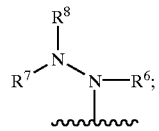

wherein $R^7$ and $R^8$ are taken together with the nitrogen to which they are attached to form a 3- to 8-membered heterocyclic ring radical; preferably a 5- to 6-membered heterocyclic ring radical; wherein said 3- to 8-membered heterocyclic ring radical may optionally contain at least one nitrogen or one oxygen heteroatom in addition to said nitrogen to which $R^7$ and $R^8$ are attached; preferably said 3- to 8-membered heterocyclic ring radical is selected from the group consisting of imidazolidin-1-yl, piperazin-1-yl, piperazin-1-yl, morpholin-4-yl, azepan-1-yl, piperidin-1-yl, and 1,3,4-triazol-1-yl;

wherein said 3- to 8-membered heterocyclic ring radical made up of $R^7$ and $R^8$ may optionally be substituted on any ring carbon atom by one to three $(C_1-C_6)$alkyl; preferably methyl; substituents per ring;

wherein said 3- to 8-membered heterocyclic ring radical made up of $R^7$ and $R^8$ may also optionally be substituted on any ring carbon atom by at least one oxo substituent per ring.

In another embodiment of the process of the invention, $R^2$ is a radical selected from the group consisting of H, —$NO_2$, —CN, and $(C_1-C_6)$alkyl optionally substituted by one —OH or by one to three fluoro substituents; preferably $R^2$ is $(C_1-C_6)$alkyl optionally substituted by one —OH or by one to three fluoro substituents; more preferably $R^2$ is —$CF_3$ or —$CHF_2$.

In another embodiment of the process of the invention, $R^2$ is a radical selected from the group consisting of $(C_2-C_6)$ alkenyl, $(C_2-C_6)$alkynyl, $(C_3-C_7)$cycloalkyl, $(C_6-C_{10})$aryl, $(C_1-C_9)$heteroaryl, and $(C_1-C_9)$heterocyclyl.

In another embodiment of the process of the invention, $R^2$ is a radical selected from the group consisting of $(C_1-C_6)$alkyl-O—, $(C_3-C_7)$cycloalkyl-O—, $(C_6-C_{10})$aryl-O—, $(C_1-C_9)$heteroaryl-O—, and $(C_1-C_9)$heterocyclyl-O—.

In another embodiment of the process of the invention, $R^2$ is a radical selected from the group consisting of H—(C=O)—, $(C_1-C_6)$alkyl-(C=O)—, $(C_3-C_7)$cycloalkyl-(C=O)—, $(C_6-C_{10})$aryl-(C=O)—, $(C_1-C_9)$heteroaryl-(C=O)—, and $(C_1-C_9)$heterocyclyl-(C=O)—.

In another embodiment of the process of the invention, $R^2$ is a radical selected from the group consisting of $(C_1-C_6)$alkyl-O—(C=O)—, $(C_3-C_7)$cycloalkyl-O—(C=O)—, $(C_6-C_{10})$aryl-O—(C=O)—, $(C_1-C_9)$heteroaryl-O—(C=O)—, and $(C_1-C_9)$heterocyclyl-O—(C=O)—.

In another embodiment of the process of the invention, $R^2$ is a radical selected from the group consisting of $(C_1-C_6)$alkyl-(C=O)—O—, $(C_3-C_7)$cycloalkyl-(C=O)—O—, $(C_6-C_{10})$aryl-(C=O)—O—, $(C_1-C_9)$heteroaryl-(C=O)—O—, and $(C_1-C_9)$heterocyclyl-(C=O)—O—.

In another embodiment of the process of the invention, $R^2$ is a radical selected from the group consisting of $(C_1-C_6)$alkyl-(C=O)—NH—, $(C_3-C_7)$cycloalkyl-(C=O)—NH—, $(C_6-C_{10})$aryl-(C=O)—NH—, $(C_1-C_9)$heteroaryl-(C=O)—NH—, $(C_1-C_9)$heterocyclyl-(C=O)—NH—, and $(C_1-C_6)$alkyl-O—(C=O)—NH—.

In another embodiment of the process of the invention, $R^2$ is a radical selected from the group consisting of $(C_1-C_6)$alkyl-NH—, $[(C_1-C_6)$alkyl$]_2$-N—, $(C_3-C_7)$cycloalkyl-NH—, $[(C_3-C_7)$cycloalkyl$]_2$-N—, $[(C_6-C_{10})$aryl]-NH—, $[(C_6-C_{10})$aryl$]_2$-N—, $[(C_1-C_6)$alkyl]-$[((C_6-C_{10})$aryl)-N]$—, $[(C_1-C_9)$heteroaryl]-NH—, $[(C_1-C_9)$heteroaryl$]_2$-N—, $[(C_1-C_9)$heterocyclyl]-NH—, and $[(C_1-C_9)$heterocyclyl$]_2$-N—.

In another embodiment of the process of the invention, $R^2$ is a radical selected from the group consisting of $H_2N$—(C=O)—, HO—NH—(C=O)—, and $(C_1-C_6)$alkyl-O—NH—(C=O)—.

In another embodiment of the process of the invention, $R^2$ is a radical selected from the group consisting of $[(C_1-C_6)$alkyl]-NH—(C=O)—, $[(C_1-C_6)$alkyl$]_2$-N—(C=O)—, $[(C_3-C_7)$cycloalkyl]-NH—(C=O)—, $[(C_3-C_7)$cycloalkyl$]_2$-N—(C=O)—, $[(C_6-C_{10})$aryl]-NH—(C=O)—, $[(C_6-C_{10}$aryl$]_2$-N—(C=O)—, $[(C_1-C_6)$alkyl]-$[((C_6-C_{10})$aryl)-N]$—(C=O)—, $[(C_1-C_9)$heteroaryl]-NH—(C=O)—, $[(C_1-C_9)$heteroaryl$]_2$-N—(C=O)—, $[(C_1-C_9)$heterocyclyl]-NH—(C=O)—, and $(C_1-C_6)$alkyl-S—.

In a preferred embodiment of the process of the invention, the ring of the formula $(R^5)$-A-$(SO_mR^4)$ is of the formula

A1

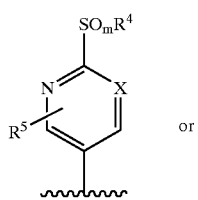

or

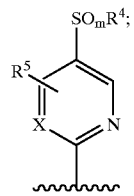

wherein X is preferably >CH and m is preferably 2.

In another embodiment of the process of the invention, the ring of the formula $(R^5)$-A-$(SO_mR^4)$ is of the formula

A3

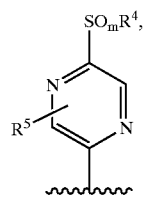

A4

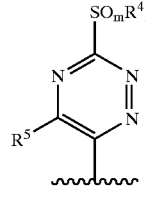

A5

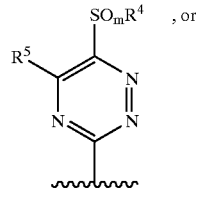, or

A6

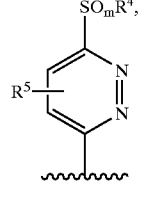

wherein m is 0, 1 or 2, preferably m is 2.

In another preferred embodiment of the process of the invention, the ring of the formula $(R^5)$-A-$(SO_mR^4)$ is of the formula

A7

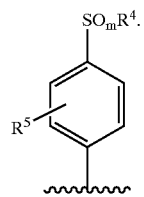

In another embodiment of the process of the invention, $R^1$ is a radical selected from the group consisting of H, —$NO_2$, and —CN, preferably $R^1$ is —CN.

In another embodiment of the process of the invention, $R^1$ is a radical selected from the group consisting of $(C_1-C_6)$alkyl, $(C_1-C_6)$alkyl-$SO_2$—, and $(C_6-C_{10})$aryl-$SO_2$—.

In another embodiment of the process of the invention, $R^1$ is a radical selected from the group consisting of H—(C=O)—, $(C_1-C_6)$alkyl-(C=O)—, $(C_1-C_6)$alkyl-O—(C=O)—, $(C_1-C_9)$heteroaryl-(C=O)—, and $(C_1-C_9)$heterocyclyl-(C=O)—.

In another embodiment of the process of the invention, $R^1$ is a radical selected from the group consisting of $H_2N$—(C=O)—, $(C_1-C_6)$alkyl-NH—(C=O)—, $[(C_1-C_6)$alkyl$]_2$-N—(C=O)—, $[(C_6-C_{10})$aryl]-NH—(C=O)—, $[(C_1-C_6)$alkyl]-$[((C_6-C_{10})$aryl)-N]—(C=O)—, HO—NH—(C=O)—, and $(C_1-C_6)$alkyl-O—NH—(C=O)—.

In a preferred embodiment of the process of the invention, $R^4$ is a radical selected from the group consisting of —$NH_2$ and $(C_1-C_6)$alkyl optionally substituted by one to four —OH substituents; more preferably $R^4$ is $(C_1-C_6)$alkyl optionally substituted by one —OH substituents; most preferably $R^4$ is methyl or 2-hydroxyethyl.

In another embodiment of the process of the invention, $R^4$ is $(C_1-C_6)$alkyl-NH— or $[(C_1-C_6)$alkyl$]_2$-N—.

In another embodiment of the process of the invention, $R^4$ is a radical selected from the group consisting of $(C_1-C_6)$alkyl-(C=O)—NH—, $(C_6-C_{10})$aryl-(C=O)—NH—, $[(C_6-C_{10})$aryl$(C_1-C_6)$alkyl]-(C=O)—NH—, $(C_1-C_6)$alkyl-O—(C=O)—NH—, $(C_6-C_{10})$aryl-O—(C=O)—NH—, $[(C_1-C_6)$alkyl]-NH—(C=O)—NH—, $[(C_1-C_6)$alkyl$]_2$-N—(C=O)—NH—, and $[(C_6-C_{10})$aryl]-NH—(C=O)—NH—.

In another embodiment of the process of the invention, $R^4$ is a radical selected from the group consisting of $[(C_1-C_6)$alkyl]-NH—HC=N—, $[C_1-C_6)$alkyl$]_2$N—HC=N—, and $[(C_6-C_{10})$aryl]-NH—HC=N—.

In another embodiment of the process of the invention, $R^5$ is a radical selected from the group consisting of H, halo, —OH, and $(C_1-C_6)$alkyl optionally substituted by one to four fluoro substituents; preferably $R^5$ is a radical selected from the group consisting of H, bromo, chloro, fluoro, $CF_3$, and methyl; more preferably $R^5$ is H.

In another embodiment of the process of the invention, $R^5$ is a radical selected from the group consisting of $(C_1-C_6)$alkyl-O—, $(C_2-C_6)$alkenyl, $(C_2-C_6)$alkynyl, $(C_3-C_7)$cycloalkyl, and —CN.

In another embodiment of the process of the invention, $R^5$ is a radical selected from the group consisting of H—(C=O)—, $(C_1-C_6)$alkyl-(C=O)—, $(C_1-C_6)$alkyl-(C=O)—O—, HO—(C=O)—, and $(C_1-C_6)$alkyl-O—(C=O)—.

In another embodiment of the process of the invention, $R^5$ is selected from the group consisting of $(C_1-C_6)$alkyl-NH—, $[(C_1-C_6)$alkyl$]_2$-N—, $(C_3-C_7)$cycloalkyl-NH—, $(C_6-C_{10})$aryl-NH—, $[(C_1-C_6)$alkyl]-$[((C_6-C_{10})$aryl)-N]—, and $(C_1-C_9)$heteroaryl-NH—.

In another embodiment of the process of the invention, $R^5$ is selected from the group consisting of $H_2N$—(C=O)—, $(C_1-C_6)$alkyl-NH—(C=O)—, $[(C_1-C_6)$alkyl$]_2$-N—(C=O)—, $(C_6-C_{10})$aryl-(C=O)—, $[(C_1-C_6)$alkyl]-$[((C_6-C_{10})$aryl)-N]—(C=O)—, $(C_1-C_6)$alkyl-O—NH—(C=O)—, and $(C_1-C_6)$alkyl-S—.

In a more preferred embodiment of the process of the invention, said fluoride containing salt contains a cationic metal selected from the group consisting of potassium and cesium; wherein 1 to 10 equivalents of said fluoride containing salt relative to the compound of the formula I is used; wherein said process is performed at a temperature of about 10° C. to about 30° C.; most preferably about at 25° C.; wherein said process is performed in the presence of a solvent selected from the group consisting of dimethylsulfoxide, dimethylformamide, dimethylacetamide, acetone and acetonitrile; most preferably dimethylsulfoxide; wherein $R^3$ is a radical selected from the group consisting of

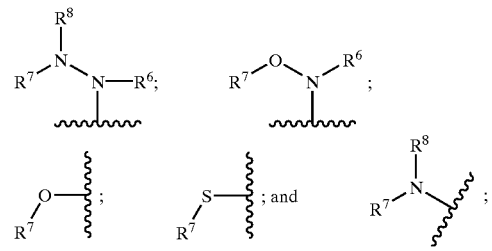

wherein $R^6$, $R^7$, and $R^8$ are as defined above.

In another more preferred embodiment of the process of the invention, said fluoride containing salt is tetrabutylammonium fluoride or cetyltrimethylammonium fluoride; wherein 0.1 to 2 equivalents of said fluoride containing salt relative to the compound of the formula I is used; wherein said process is performed at a temperature of about 20° C. to about 80° C.; most preferably at about 25° C.; wherein said process is performed in the presence of a solvent selected from the group consisting of acetonitrile, dichloromethane, chloroform, tetrahydrofuran and dichloroethane; most preferably tetrahydrofuran; wherein $R^3$ is a radical selected from the group consisting of

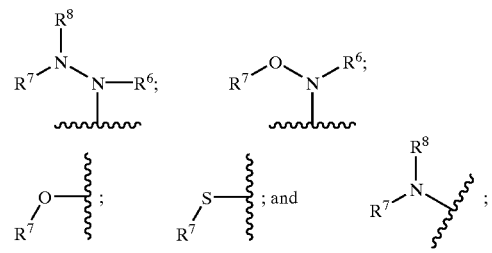

wherein $R^6$, $R^7$, and $R^8$ are as defined above.

Examples of specific preferred compounds of the formula I prepared by the process of the present invention are the following:

1-(5-Methanesulfonyl-pyridin-2-yl)-5-(4-methylene-cyclohexylmethoxy)-3-trifluoromethyl-1H-pyrazole-4-carbonitrile;

5-(2-Fluoro-benzylsulfanyl)-1-(5-methanesulfonyl-pyridin-2-yl)-3-trifluoromethyl-1H-pyrazole-4-carbonitrile;

6-[4-cyano-3-difluoromethyl-5-(3,5-cis-dimethyl-piperidin-1-yl)-pyrazol-1-yl]-pyridine-3-sulfonic acid amide;

6-[4-cyano-5-(2,2-dimethyl-propoxy)-3-trifluoromethyl-pyrazol-1-yl]-pyridine-3-sulfonic acid amide;

3-Difluoromethyl-5-(cis-2,6-dimethyl-morpholin-4-yl)-1-(5-methanesulfonyl-pyridin-2-yl)-1H-pyrazole-4-carbonitrile;

5-Cyclopentylamino-3-difluoromethyl-1-(4-methanesulfonyl-phenyl)-1H-pyrazole-4-carbonitrile;
5-(N'-Ethyl-N'-methyl-hydrazino)-1-(5-methanesulfonyl-pyridin-2-yl)-3-trifluoromethyl-1H-pyrazole-4-carbonitrile;
5-tert-Butoxyamino-1-(5-methanesulfonyl-pyridin-2-yl)-3-trifluoromethyl-1H-pyrazole-4-carbonitrile;
5-Azepan-1-yl-1-(5-methanesulfonyl-pyridin-2-yl)-3-trifluoromethyl-1H-pyrazole-4-carbonitrile;
6-[4-Cyano-5-(3,5-dimethyl-piperidin-1-yl)-3-trifluoromethyl-pyrazol-1-yl]-pyridine-3-sulfonic acid acetyl-amide;
6-[4-Cyano-5-(3,5-dimethyl-piperidin-1-yl)-3-trifluoromethyl-pyrazol-1-yl]-pyridine-3-sulfonic acid propionyl-amide;
6-[4-Cyano-5-(3,5-dimethyl-piperidin-1-yl)-3-trifluoromethyl-pyrazol-1-yl]-pyridine-3-sulfonic acid isobutyryl-amide;
6-[4-Cyano-5-(3,5-dimethyl-piperidin-1-yl)-3-trifluoromethyl-pyrazol-1-yl]-pyridine-3-sulfonic acid (2,2-dimethyl-propionyl)-amide;
6-[4-Cyano-5-(3,5-dimethyl-piperidin-1-yl)-3-trifluoromethyl-pyrazol-1-yl]-pyridine-3-sulfonic acid (1,1-dimethyl)-ethoxycarbonyl-amide;
6-[4-Cyano-5-(3,5-dimethyl-piperidin-1-yl)-3-trifluoromethyl-pyrazol-1-yl]-pyridine-3-sulfonic acid (3-methyl-butyryl)-amide;
6-[4-Cyano-5-(2,2-dimethyl-propylamino)-3-trifluoromethyl-pyrazol-1-yl]-pyridine-3-sulfonic acid acetyl-amide;
6-[4-Cyano-5-(2,2-dimethyl-propylamino)-3-trifluoromethyl-pyrazol-1-yl]-pyridine-3-sulfonic acid propionyl-amide;
6-[4-Cyano-5-(2,2-dimethyl-propylamino)-3-trifluoromethyl-pyrazol-1-yl]-pyridine-3-sulfonic acid isobutyryl-amide;
6-[4-Cyano-5-(2,2-dimethyl-propylamino)-3-trifluoromethyl-pyrazol-1-yl]-pyridine-3-sulfonic acid (2,2-dimethyl-propionyl)-amide;
6-[4-Cyano-5-(2,2-dimethyl-propylamino)-3-trifluoromethyl-pyrazol-1-yl]-pyridine-3-sulfonic acid (1,1-dimethyl)-ethoxycarbonyl-amide;
6-[4-Cyano-5-(2,2-dimethyl-propylamino)-3-trifluoromethyl-pyrazol-1-yl]-pyridine-3-sulfonic acid (3-methyl-butyryl)-amide;
6-[4-Cyano-3-difluoromethyl-5-(2,6-cis-dimethyl-morpholin-4-yl)-pyrazol-1-yl]-pyridine-3-sulfonic acid acetyl-amide;
4-[4-Cyano-3-difluoromethyl-5-(2,6-dimethyl-morpholin-4-yl)-pyrazol-1-yl]-N-propionyl-benzenesulfonamide;
6-[4-Cyano-5-(2,6-dimethyl-morpholin-4-yl)-3-trifluoromethyl-pyrazol-1-yl]-pyridine-3-sulfonic acid isobutyryl-amide; and
5-Azepan-1-yl-1-(4-methanesulfonyl-phenyl)-3-trifluoromethyl-1H-pyrazole-4-carbonitrile; or
the pharmaceutically acceptable salts thereof.

DETAILED DESCRIPTION OF THE INVENTION

The new process synthesis is shown in reaction schemes below. Unless otherwise indicated, the ring of the formula $(R^5)$-A-$(SO_mR^4)$, m, and $R^1$ through $R^{10}$ in the reaction schemes and discussion that follow are as defined above.

Scheme 1

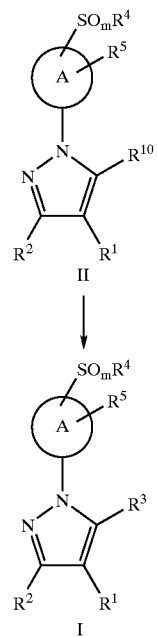

Scheme 2

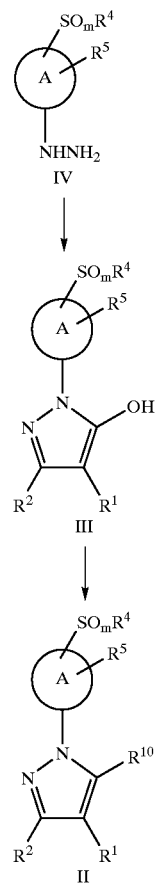

Scheme 1 refers to the preparation of a compound of formula I.

Referring to Scheme 1, a compound of formula I (i.e., a compound of the formulae IA1–IA7, respectively):

can be prepared by reacting a compound of formula II, i.e., a compound of formulae IIA1–IIA7, respectively:

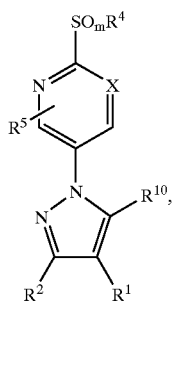

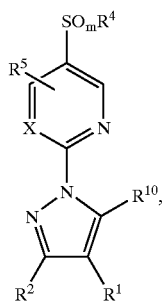

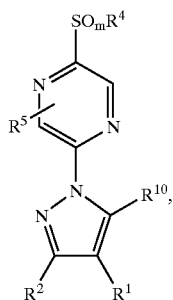

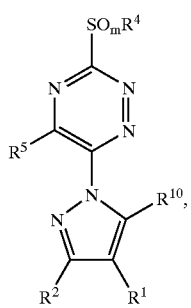

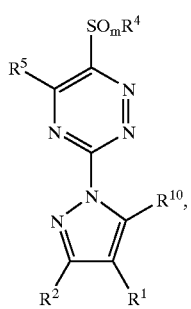

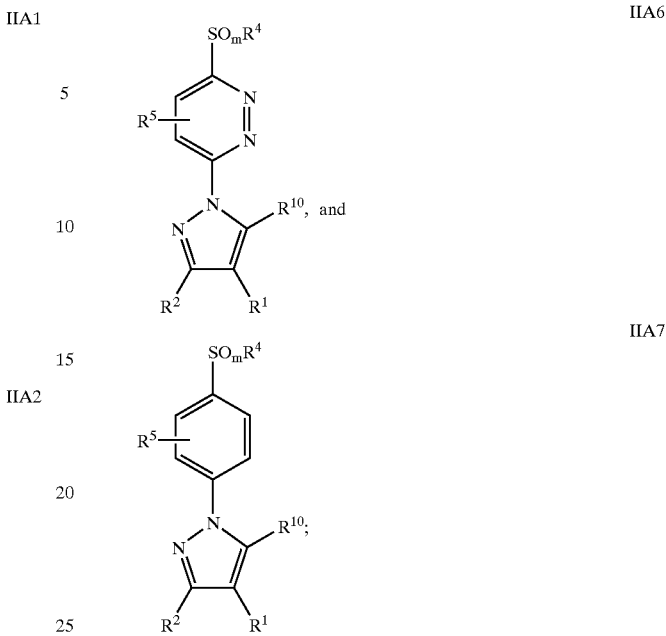

wherein $R^{10}$ is a leaving group, with a compound of the formula $R^3$—H in the presence of a fluoride containing salt and in the presence of a solvent.

Suitable leaving groups $R^{10}$ of the compound of formula II include halo, such as fluoro, chloro, iodo, or bromo; $(C_1-C_6)$alkyl-$SO_3$—, such as $CH_3$—$SO_3$—, $CF_3$—$SO_3$—, or $CF_3CF_2$—$SO_3$—; $(C_6-C_{10})$aryl-$SO_3$—, such as tosyl-$SO_3$— or phenyl-$SO_3$—; $(C_1-C_6)$alkyl-$SO_2$—, such as $CH_3$—$SO_2$—; or $(C_6-C_{10})$aryl-$SO_2$—, such as phenyl-$SO_2$—. Preferably, the leaving group $R^{10}$ is halo, such as chloro; or $(C_1-C_6)$alkyl-$SO_3$—, such as $CF_3$—$SO_3$—, or $CF_3CF_2$—$SO_3$—.

Suitable fluoride containing salts used in process of the invention include a metal salt, such as lithium, sodium, potassium, cesium, magnesium, calcium, strontium, and barium; tetra$(C_1-C_8)$alkylammonium fluoride, such a tetrabutylammonium fluoride; or $(C_1-C_{16})$alkyltri$(C_1-C_2)$alkylammonium fluoride, such as cetyltrimethylammonium fluroide.

The process of the invention can be performed in the presence of about 0.05 to about 10 equivalents; more preferably about 0.05 to about 5 equivalents; most preferably about 0.1 to about 2 equivalents; of the fluoride containing salts relative to the compound of formula I.

Suitable solvents used in the process of the invention include acetonitrile, dichloromethane, chloroform, tetrahydrofuran, dichloroethane, dimethylsulfoxide, dimethylformamide, dimethylacetamide, or acetone.

The process of the invention can be conducted at a temperature of about 10° C. to about 100° C., preferably about 20° C. to about 80° C. The process of the invention can be conducted for a period from about 2 hours to about 96 hours, preferably from about 12 hours to about 48 hours.

When the fluoride containing salt is a metal salt such as potassium fluoride or cesium fluoride; the suitable solvents include dimethylsulfoxide, dimethylformamide, dimethylacetamide, acetone, or acetonitrile; the temperature is preferably about 10° C. to about 30° C.; and in the presence of about 0.05 to about 5 equivalents of the fluoride containing salts relative to the compound of formula I.

When the fluoride containing salt is tetra($C_1$–$C_8$)alkylammonium fluoride or ($C_1$–$C_{16}$)alkyltri($C_1$–$C_2$)alkylammonium fluoride; the suitable solvents include acetonitrile, dichloromethane, chloroform, tetrahydrofuran, or dichloroethane; and the temperature is preferably about 20° C. to about 80° C.; and in the presence of about 0.1 to about 2 equivalents of the fluoride containing salts relative to the compound of formula I.

Scheme 2 illustrates methods of preparing compounds of the formula II, as defined above.

Referring to Scheme 2, a compound of the formula II wherein $R^{10}$ is halo can be prepared by reacting a compound of the formula III with a halogenating agent in a polar solvent. Suitable halogenating agents include oxalyl chloride, $POCl_3$, $POBr_3$, $SOCl_2$ or $PCl_5$, preferably $POCl_3$. Suitable solvents include methylene chloride, N,N-dimethylformamide (DMF), N,N-dimethylacetamide (DMA) or N-methyl-2-pyrrolidinone (NMP), preferably methylene chloride. The aforesaid reaction is generally carried out at a temperature from about 20° C. to about 140° C., preferably at about the reflux temperature of the polar solvent, preferably when the solvent is methylene chloride, the temperature is 55° C. The aforesaid reaction is generally carried out for a period from about 1 hour to about 48 hours, preferably about 2 hours to about 24 hours.

A compound of the formula II wherein $R^{10}$ contains a —$SO_3$— component, such as ($C_1$–$C_6$)alkyl-$SO_3$— or ($C_6$–$C_{10}$)aryl-$SO_3$—, can be prepared by reacting a compound of the formula with a sulfonylating agent in a polar solvent. Suitable sulfonylating agents include trifluoromethanesulfonic anhydride, methanesulfonyl chloride, or methanesulfonyl anhydride, preferably methanesulfonyl chloride. Suitable solvents for the aforesaid reaction include methylene chloride, N,N-dimethylformamide (DMF), N,N-dimethylacetamide (DMA) or N-methyl-2-pyrrolidinone (NMP), preferably methylene chloride. The aforesaid reaction is generally carried out at a temperature from about −10° C. to about 25° C., preferably at about 0° C. The aforesaid reaction is generally carried out for a period from about 1 hour to about 48 hours.

A compound of the formula II wherein said $R^{10}$ contains a —$SO_2$— component, such as ($C_1$–$C_6$)alkyl-$SO_2$— or ($C_6$–$C_{10}$)aryl-$SO_2$—, can be prepared by reacting a compound of the formula II wherein $R^{10}$ is halo or contains a —$SO_3$— component, as defined above, with a sulfonating agent in a polar solvent. Suitable sulfonating agents include $NaSO_3CH_3$ or $NaSO_3$($C_6$–$C_{10}$)aryl. Other suitable sulfonating agents include NaS($C_1$–$C_6$)alkyl, such as $NaSCH_3$, or NaS($C_6$–$C_{10}$)aryl, such as NaS($C_6H_5$), followed by an oxidizing agent, such as OXONE®, metachloroperbenzoic acid, or hydrogen peroxide. Suitable solvents for the aforesaid reaction include DMF, DMA, or DMSO, preferably DMSO. The aforesaid reaction is generally carried out at a temperature from about minus 10° C. to about 120° C., preferably at about 100° C. The aforesaid reaction is generally carried out for a period from about 1 hour to about 48 hours, preferably about 2 hours to about 24 hours.

Compounds of the formula III can be prepared by reacting a compound of formula IV, wherein the ring of the formula ($R^5$)-A-($SO_mR^4$) is as defined above, with a reagent of the formula

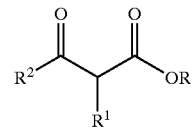

wherein R is ($C_1$–$C_6$)alkyl, such as methyl; in a suitable solvent under acidic, neutral or basic conditions. Preferably, the reagent is 4,4,4-trifluoro-3-oxo-butyric acid methyl ester. Suitable solvents include methanol, ethanol, DMF, DMSO, water or a mixture thereof. Suitable acids include hydrochloric acid or trifluoroacetic acid. Suitable bases include sodium hydroxide, potassium hydroxide, and potassium carbonate. The aforesaid reaction is generally carried out at a temperature from about 0° C. to about 140° C., preferably at about 20° C. to about 100° C. most preferably at about 20° C. to about 100° C. The aforesaid reaction is generally carried out for a period from about 1 hour to about 24 hours, preferably from about 6 hours to about 16 hours.

The above reagents of formula $R^2$—(C=O)—CH($R^1$)—(C=O)—OR are commercially available or can be prepared according to the methods described in Jerry March, "Advanced Organic Chemistry", 4th edition, 1992, and references cited therein.

Compounds of formula IV are commercially available or can be made by methods well known to those of ordinary skill in the art or according to the methods of Scheme 3. For example, compounds of formula IV can be prepared by the method described in Vavrina, et al., Collection Czechoslov. Chem. Commun., Vol. 37, 1721 (1972), which is incorporated herein by reference.

Scheme 3 refers to a preparation of a compound of the formula IV.

Referring to Scheme 3, a compound of the formula IV (i.e., a compound of the formulae IVA1–IVA7, respectively):

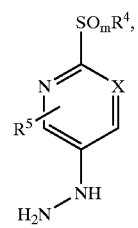

IVA1

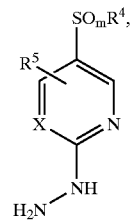

IVA2

-continued

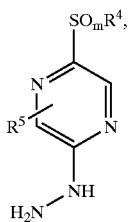
IVA3

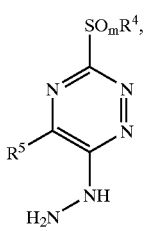
IVA4

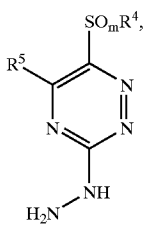
IVA5

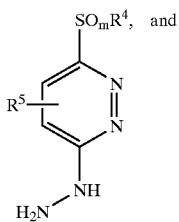
IVA6

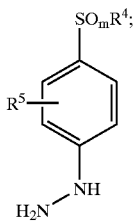
IVA7 wherein m is 1 or 2, can be prepared by reacting a compound of the formula V (i.e., a compound of the formulae VA1–VA7, respectively):

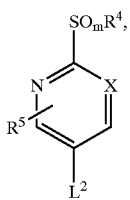
VA1

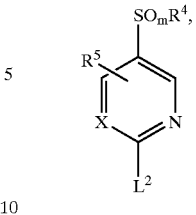
VA2

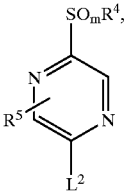
VA3

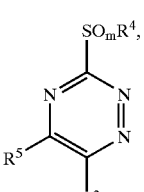
VA4

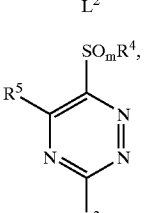
VA5

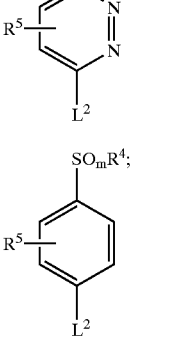
VA6

VA7 wherein $L^2$ is a leaving group and m is 1 or 2, with hydrazine (preferably anhydrous hydrazine) in the presence of a polar solvent. Suitable leaving groups $L^2$ include halo, triflate, or methylsulfonyl, preferably halo, such as chloro and bromo. Suitable solvents include alcohol (such as ethanol, methanol, propanol or butanol), DMSO, DMF, DMA, or NMP, preferably alcohol, most preferably ethanol. This reaction can be carried out at a temperature from about 0° C. to about 140° C., preferably at about the reflux temperature of the solvent. This reaction can be carried out for a period of from about 1 hour to about 36 hours, preferably from about 2 hours to about 24 hours. Preferably the product is isolated as a salt, such as a hydrobromide or hydrochloride salt. The hydrochloride salt is preferred.

The compound of the formula IV wherein m is 0 can be prepared by reacting a compound of the formula VI (i.e., a compound of the formulae VIA1–VIA7, respectively):

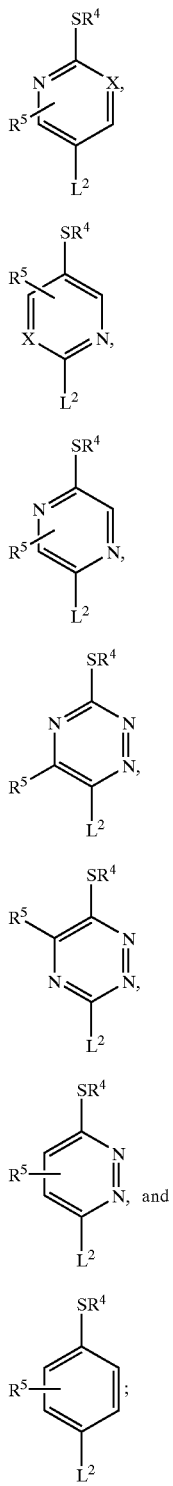

wherein $L^2$ is a leaving group, with hydrazine (preferably anhydrous hydrazine) in the presence of a polar solvent, under the condition described in the aforesaid paragraph.

The compound of the formula V (i.e., a compound of the formulae VA1–VA7, respectively, as defined above) can be prepared by reacting a compound of the formula VI (i.e., a compound of the formulae VIA1–VIA7, respectively, as defined above), wherein $L^2$ is a leaving group, with an oxidizing reagent in the presence of a solvent. Suitable oxidizing agents include meta-chloroperbenzoic acid, hydrogen peroxide, sodium perborate, or OXONE®, preferably OXONE®. Suitable solvents or solvent mixtures include methanol-water, dioxane-water, tetrahydrofuran-water, methylene chloride, or chloroform, preferably methanol-water or methylene chloride. The aforesaid reaction can be carried out at a temperature from about 0° C. to about 60° C., preferably the temperature may range from about 20° C. to about 25° C. (i.e. room temperature). The aforesaid reaction can be carried out for a period of from about 0.5 hours to about 24 hours, preferably about 16 hours.

The compounds of the formula VI (i.e., a compound of the formulae VIA1–VIA7, respectively, as defined above) can be prepared from a compound of formula VII (i.e., a compound of the formulae VIIA1–VIIA7, respectively):

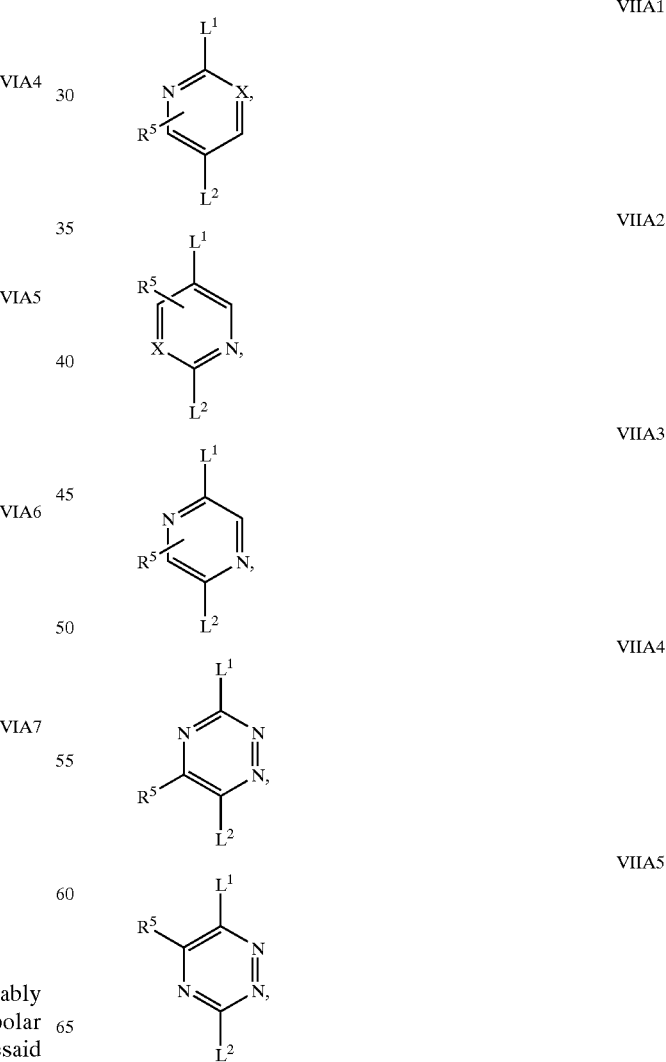

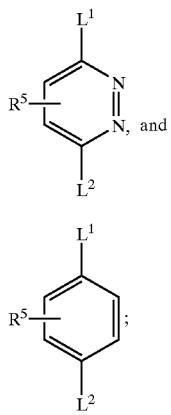

wherein each of $L^1$ and $L^2$ independently is a leaving group, by reacting said compound of formula VII with a sulfur reagent in the presence or absence of a base in a polar solvent. Suitable leaving groups $L^1$ include halo or methyl-SO$_2$—, preferably halo, such as bromo or iodo. Suitable leaving groups $L^2$ halo or methyl-SO$_2$—, preferably halo, such as bromo or iodo. Suitable sulfur reagents include ($C_1$–$C_6$)alkyl-SH, ($C_1$–$C_6$)alkyl-S—S—($C_1$–$C_6$)alkyl, ($C_1$–$C_6$)alkyl-SO$_3$—, Na—S—($C_1$–$C_6$)alkyl or K—S—($C_1$–$C_6$)alkyl. Suitable bases include sodium hydroxide, triethylamine, alkyllithiums (such as n-butyllithium, sec-butyllithium, and tert-butyllithium) and lithium diisopropylamide. Suitable solvents include dialkylethers (such as dimethylether), alcohol (such as methanol, ethanol and tert-butanol), THF, benzene, toluene, xylene, DMF, DMSO, dioxane, 1,2-dimethoxyethane, and a mixture of an alcohol and water. This reaction can be carried out at a temperature from about −78° C. to 200° C., preferably the temperature may range from about −78° C. to about 120° C. The reaction can be carried out for a period of from about 1 minute to about 24 hours.

Compounds of the formula VII (i.e., a compound of the formulae VIIA1–VIIA7, respectively, as defined above) may be prepared by methods well known to those of ordinary skill in the art (see for example, EP 1104760).

Unless indicated otherwise, the pressure of each of the above reactions is not critical. Generally, the reactions will be conducted at a pressure of about one to about three atmospheres, preferably at ambient pressure (about one atmosphere).

Those skilled in the art will appreciate that the above schemes describe general methods for preparing the compounds of the invention. Specific compounds of formula I may possess sensitive functional groups that require protecting groups when prepared with the intermediates described. Examples of suitable protecting groups may be found in T. W. Greene and P. Wuts, Protecting Groups in Organic Synthesis, John Wiley & Sons, 2nd Edition, New York, 1991.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations and then evaporating the resulting solution to dryness, preferably under reduced pressure. Alternatively, they may also be prepared by mixing lower alkanolic solutions of the acidic compounds and the desired alkali metal alkoxide together and then evaporating the resulting solution to dryness in the same manner as before. In either case, stoichiometric quantities of reagents are preferably employed in order to ensure completeness of reaction and maximum product yields.

The compounds of formula I of the invention can be used in a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (such as in a mammal, preferably a human, cat, livestock or a dog, comprising an amount of a compound of formula I or a pharmaceutically acceptable salt thereof effective in such treatment and a pharmaceutically acceptable carrier.

The compounds of formula I of the invention can also be used in a pharmaceutical composition for the treatment of a disorder or condition that can be treated by selectively inhibiting COX-2 in a mammal, preferably a human, cat, livestock or dog, comprising an effective amount of a compound of formula I or a pharmaceutically acceptable salt thereof and a pharmaceutically acceptable carrier.

The compounds of formula I of the invention can also be used in a pharmaceutical composition for the treatment of a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The compounds of formula I of the invention can also be used in a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain and cancer) in a mammal, preferably a human, cat, livestock or a dog, comprising administering to said mammal an amount of a compound of formula I or a pharmaceutically acceptable salt thereof effective in treating such a condition.

The compounds of formula I of the invention can also be used in a method for treating a disorder or condition that can be treated by selectively inhibiting COX-2 in a mammal, preferably a human, cat, livestock or a dog, comprising administering to a mammal requiring such treatment a COX-2 selective inhibiting effective amount of a compound of formula I or a pharmaceutically acceptable salt thereof.

Method for Assessing Biological Activities

The activity of the compounds of the formula I of the present invention may be demonstrated by the following assays.

Human In Vitro Assays

Human Cell-Based COX-1 Assay

Human peripheral blood obtained from healthy volunteers can be diluted to $\frac{1}{10}$ volume with 3.8% sodium citrate solution. The platelet-rich plasma immediately obtained can be washed with 0.14 M sodium chloride containing 12 mM Tris-HCl (pH 7.4) and 1.2 mM EDTA. Platelets can then be washed with platelet buffer (Hanks buffer (Ca free) containing 0.2% BSA and 20 mM Hepes). Finally, the human washed platelets (HWP) can be suspended in platelet buffer at the concentration of $2.85 \times 10^8$ cells/ml and stored at room temperature until use. The HWP suspension (70 µl aliquots, final $2.0 \times 10^7$ cells/ml) can be placed in a 96-well U bottom plate and 10 µl aliquots of 12.6 mM calcium chloride added. Platelets can be incubated with A23187 (final 10 µM, Sigma) with test compound (0.1–100 µM) dissolved in DMSO (final concentration; less than 0.01%) at 37° C. for 15 minutes. The reaction can be stopped by addition of EDTA (final 7.7 mM) and TxB2 in the supernatant quantitated by using a radioimmunoassay kit (Amersham) according to the manufacturer's procedure.

Human Cell-Based COX-2 Assay

The human cell based COX-2 assay can be carried out as previously described (Moore et al., *Inflam. Res.*, 45, 54, 1996). Confluent human umbilical vein endothelial cells (HUVECs, Morinaga) in a 96-well flat bottom plate can be washed with 80 ml of RPMI1640 containing 2% FBS and incubated with hIL-1β (final concentration 300 U/ml, R & D Systems) at 37° C. for 24 hours. After washing, the activated HUVECs can be incubated with test compound (final concentration; 0.1 nM–1 µM) dissolved in DMSO (final concentration; less than 0.01%) at 37° C. for 20 minutes and stimulated with A23187 (final concentration 30 mM) in Hanks buffer containing 0.2% BSA, 20 mM Hepes at 37° C. for 15 minutes. 6-Keto-PGF$_{1\alpha}$, stable metabolite of PGI2, in the supernatant can be quantitated by using a radioimmunoassay method (antibody; Preseptive Diagnostics, SPA; Amersham).

Canine In Vitro Assays

The following canine cell based COX 1 and COX-2 assays have been reported in Ricketts et al., *Evaluation of Selective Inhibition of Canine Cyclooxygenase 1 and 2 by Carprofen and Other Nonsteroidal Anti-inflammatory Drugs*, American Journal of Veterinary Research, 59 (11), 1441–1446.

Protocol for Evaluation of Canine COX-1 Activity

Test drug compounds can be solubilized and diluted the day before the assay can be to be conducted with 0.1 mL of DMSO/9.9 mL of Hank's balanced salts solution (HBSS) and stored overnight at 4° C. On the day that the assay can be carried out, citrated blood can be drawn from a donor dog, centrifuged at 190×g for 25 minutes at room temperature and the resulting platelet-rich plasma can be then transferred to a new tube for further procedures. The platelets can be washed by centrifuging at 1500×g for 10 minutes at room temperature. The platelets can be washed with platelet buffer comprising Hank's buffer (Ca free) with 0.2% bovine serum albumin (BSA) and 20 mM HEPES. The platelet samples can then be adjusted to $1.5 \times 10^7$/mL, after which 50 µl of calcium ionophore (A23187) together with a calcium chloride solution can be added to 50 µl of test drug compound dilution in plates to produce final concentrations of 1.7 µM A23187 and 1.26 mM Ca. Then, 100 µl of canine washed platelets can be added and the samples can be incubated at 37° C. for 15 minutes, after which the reaction can be stopped by adding 20 µl of 77 mM EDTA. The plates can then be centrifuged at 2000×g for 10 minutes at 4° C., after which 50 µl of supernatant can be assayed for thromboxane B$_2$ (TXB$_2$) by enzyme-immunoassay (EIA). The pg/mL of TXB$_2$ can be calculated from the standard line included on each plate, from which it can be possible to calculate the percent inhibition of COX-1 and the IC$_{50}$ values for the test drug compounds.

Protocol for Evaluation of Canine COX-2 Activity

A canine histocytoma (macrophage-like) cell line from the American Type Culture Collection designated as DH82, can be used in setting up the protocol for evaluating the COX-2 inhibition activity of various test cells 10 µg/mL of LPS, after which the flask cultures can be incubated overnight. The same test drug compound dilutions as described above for the COX-1 protocol can be used for the COX-2 assay and can be prepared the day before the assay can be carried out. The cells can be harvested from the culture flasks by scraping and can then be washed with minimal Eagle's media (MEM) combined with 1% fetal bovine serum, centrifuged at 1500 rpm for 2 minutes and adjusted to a concentration of $3.2 \times 10^5$ cells/mL. To 50 µl of test drug dilution there can be added 50 µl of arachidonic acid in MEM to give a 10 µM final concentration and there can be added as well 100 µl of cell suspension to give a final concentration of $1.6 \times 10^5$ cells/mL. The test sample suspensions can be incubated for 1 hour and then centrifuged at 1000 rpm for 10 minutes at 4° C., after which 50 µl aliquots of each test drug sample can be delivered to EIA plates. The EIA can be performed for prostaglandin E$_2$ (PGE$_2$) and the pg/mL concentration of PGE$_2$ can be calculated from the standard line included on each plate. From this data it can be possible to calculate the percent inhibition of COX-2 and the IC$_{50}$ values for the test drug compounds. Repeated investigations of COX-1 and COX-2 inhibition can be conducted over the course of several months. The results are averaged and a single COX-1: COX-2 ratio is calculated.

Whole blood assays for COX-1 and COX-2 are known in the art such as the methods described in C. Brideau, et al., *A Human Whole Blood Assay for Clinical Evaluation of Biochemical Efficacy of Cyclooxygenase Inhibitors, Inflammation Research*, Vol. 45, pp. 68–74 (1996). These methods may be applied with feline, canine or human blood as needed.

In Vivo Assays

Carrageenan Induced Foot Edema in Rats

Male Sprague-Dawley rats (5 weeks old, Charles River Japan) can be fasted overnight. A line can be drawn using a marker above the ankle on the right hind paw and the paw volume (V0) can be measured by water displacement using a plethysmometer (Muromachi). Animals can be given orally either vehicle (0.1% methyl cellulose or 5% Tween 80) or a test compound (2.5 ml per 100 g body weight). One hour later, the animals can then be injected intradermally with -carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) can be measured and the increase in volume (V3–V0) calculated. Since maximum inhibition attainable with classical NSAIDs is 60–70%, ED$_{30}$ values can be calculated.

Gastric Ulceration in Rats

The gastric ulcerogenicity of test compound can be assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, can be given orally either vehicle (0.1% methyl cellulose or 5% Tween 80) or a test compound (1 ml per 100 g body weight). Six hours after, the animals can be sacrificed by cervical dislocation. The stomachs can be removed and inflated with 1% formalin solution (10 ml). Stomachs can be opened by cutting along the greater curvature. From the number of rats that showed at least one gastric ulcer or haemorrhaging erosion (including ecchymosis), the incidence of ulceration can be calculated. Animals did not have access to either food or water during the experiment.

Canine Whole Blood Ex Vivo Determinations of COX-1 and COX-2 Activity Inhibition The in vivo inhibitory potency of a test compound against COX-1 and COX-2 activity may be evaluated using an ex vivo procedure on canine whole blood. Three dogs can be dosed with 5 mg/kg of the test compound administered by oral gavage in 0.5% methylcellulose vehicle and three dogs can be untreated. A zero-hour blood sample can be collected from all dogs in the study prior to dosing, followed by 2- and 8-hour post-dose blood sample collections. Test tubes can be prepared containing 2 $\mu$L of either (A) calcium ionophore A23187 giving a 50 $\mu$M final concentration, which stimulates the production of thromboxane $B_2$ ($TXB_2$) for COX-1 activity determination; or of (B) lipopolysaccharide (LPS) to give a 10 $\mu$g/mL final concentration, which stimulates the production of prostaglandin $E_2$ ($PGE_2$) for COX-2 activity determination. Test tubes with unstimulated vehicle can be used as controls. A 500 $\mu$L sample of blood can be added to each of the above-described test tubes, after which they can be incubated at 37° C. for one hour in the case of the calcium ionophore-containing test tubes and overnight in incubation, 10 $\mu$L of EDTA can be added to give a final concentration of 0.3%, in order to prevent coagulation of the plasma which sometimes occurs after thawing frozen plasma samples. The incubated samples can be centrifuged at 4° C. and the resulting plasma sample of ~200 $\mu$L can be collected and stored at −20° C. in polypropylene 96-well plates. In order to determine endpoints for this study, enzyme immunoassay (EIA) kits available from Cayman can be used to measure production of $TXB_2$ and $PGE_2$, utilizing the principle of competitive binding of tracer to antibody and endpoint determination by colorimetry. Plasma samples can be diluted to approximate the range of standard amounts which would be supplied in a diagnostic or research tools kit, i.e., 1/500 for $TXB_2$ and 1/750 for $PGE_2$.

The data set out in Table 1 below show how the percent inhibition of COX-1 and COX-2 activity is calculated based on their zero hour values. The data is expressed as treatment group averages in pg/ml of $TXB_2$ and $PGE_2$ produced per sample. Plasma dilution can be not factored in said data values.

The data in Table 1 show that, in this illustration, at the 5 mg/kg dose there can be significant COX-2 inhibition at both timepoints. The data in Table 1 also show that at the 5 mg/kg dose there can be no significant inhibition of COX-1 activity at the timepoints involved. Accordingly, the data in Table 1 clearly demonstrates that at the 5 mg/kg dosage concentration this compound possesses good COX-2 selectivity.

TABLE 1

| | COX-1 ACTIVITY INHIBITION—Group Averages | | | | |
|---|---|---|---|---|---|
| | $TXB_2$ Pg/mL/Well | | | Percent Inhibition | |
| Hour | 0-hour | 2-hour | 8-hour | 2-hour | 8-hour |
| Untreated | 46 | 45 | 140 | 2% | 0% |
| 5 mg/kg | 41 | 38 | 104 | 7% | 0% |
| | COX-2 ACTIVITY INHIBITION—Group Averages | | | | |
| | $PGE_2$ Pg/mL/Well | | | Percent Inhibition | |
| Hour | 0-hour | 2-hour | 8-hour | 2-hour | 8-hour |
| Untreated | 420 | 486 | 501 | 0% | 0% |
| 5 mg/kg | 711 | 165 | 350 | 77% | 51% |

COX inhibition is observed when the measured percent inhibition is greater than that measured for untreated controls. The percent inhibition in the above table is calculated in a straightforward manner in accordance with the following equation:

$$\% \text{ Inhibition (2-hour)} = \frac{(PGE_2 \text{ at } t = 0) - (PGE_2 \text{ at } t = 2)}{(PGE_2 \text{ at } t = 0)}$$

Data Analysis

Statistical program packages, SYSTAT (SYSTAT, INC.) and StatView (Abacus Cencepts, Inc.) for Macintosh can be used. Differences between test compound treated group and control group can be tested for using ANOVA. The $IC_{50}$ (ED30) values can be calculated from the equation for the log-linear regression line of concentration (dose) versus percent inhibition.

Most compounds prepared in the Working Examples as described hereinafter can be tested by at least one of the methods described above and showed $IC_{50}$ values of 0.001 $\mu$M to 3 $\mu$M with respect to inhibition of COX-2 in either the canine or human assays.

COX-2 selectivity can be determined by ratio in terms of $IC_{50}$ value of COX-1 inhibition to COX-2 inhibition. In general, it can be said that a compound showing a COX-1/COX-2 inhibition ratio of more than 5 has good COX-2 selectivity.

The compounds of the formula I of this invention can be administered via oral, parenteral, anal, buccal or topical routes to mammals (including humans, dogs, cats, horses and livestock).

In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

These compounds are most desirably administered to said non-human mammals, e.g. dogs, cats, horses or livestock in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day and most preferably from about 0.5 mg/kg to about 8.0 mg/kg/day.

The compounds of the present invention may be administered alone or in combination with pharmaceutically acceptable carriers or diluents by either of the above routes previously indicated and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging from 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes and, if so desired, emulsifying and/or suspending agents as well, together with such diluents as water, ethanol, propylene glycol, glycerin and various combinations thereof.

A preferred composition for dogs comprises an ingestible liquid peroral dosage form selected from the group consisting of a solution, suspension, emulsion, inverse emulsion, elixir, extract, tincture and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained- and/or controlled-release of said anti-inflammatory selective COX-2 inhibitor. Such preferred compositions include all such dosage forms which produce $\geq 80\%$ inhibition of COX-2 isozyme activity and result in a plasma concentration of said inhibitor of at least 3 fold the COX-2 $IC_{50}$ for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 80\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours and most preferably for at least 24 hours. More preferably, there is included the above-described dosage forms which produce $\geq 90\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours and most preferably for at least 24 hours.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula I may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

For transdermal administration, transdermal patches prepared in accordance with well known drug delivery technology may be prepared and applied to the skin of a mammal, preferably a human or a dog, to be treated, whereafter the active agent by reason of its formulated solubility characteristics migrates across the epidermis and into the dermal layers of the skin where it is taken up as part of the general circulation, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology and may be prepared in such a way as to provide controlled-, sustained- and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

EXAMPLES

The invention is illustrated in the following non-limiting examples. Unless stated otherwise, all operations were carried out at room or ambient temperature, that is, in the range of 18–25° C.; evaporation of solvent was carried out using a rotary evaporator under reduced pressure with a bath of up to 60° C.; reactions were monitored by high performance liquid chromatography (HPLC), and reaction times are given for illustration only; melting points (m.p.) given are uncorrected (polymorphism may result in different melting points); structure and purity of all isolated compounds were assured by at least one of the following techniques: Thin Layer Chromatography (TLC) (Merck silica gel 60 F-254 precoated plates), High Pressure Liquid Chromatography (HPLC), Nuclear Magnetic Resonance (NMR), or Mass Spectrometry (MS). Flash column chromatography was carried out on Merck silica gel 60 (230–400 mesh ASTM). Preparative TLC was carried out on Whatman 1000 µM plates and/or Baker TLC plates. Preparative HPLC was carried out on Hewlett Packard 1100 Liquid Chromatography and Mass Selective Detector (LC/MS). Purification by HPLC was carried out on a 15×100 mm Monochrom 5µ CN column, with a flow rate of 20 ml/min and a running gradient of 10% to 80% of isopropanol in n-hexane. NMR data were determined on a Varian Unity Inova 400 or Varian Unity Inova 500 system using deuterated chloroform (99.8% D), methanol (99.8% D) or dimethylsulfoxide (99.9% D) as solvent unless indicated otherwise, relative to tetramethylsilane (TMS) in parts per million (ppm); conventional abbreviations used are: s=singlet, d=doublet, t=triplet, q=quartet, m=multiplet, and br=broad. MS was carried out on a Micromass ZMD mass spectrometer with Atmospheric Pressure Chemical Ionization (APCI). Analytical LC/MS was carried out using one of the following methods: MetaChem Polaris 2×20 mm C18 column, gradient from 2 to 100% of acetonitrile in 0.01% aqueous formic acid in 3.75 minutes, MS detection on Micromass ZMD with electrospray ionization (ESI); Luna 3×250 mm 5 µM C8 column, gradient from 50 to 100% of acetonitrile in 0.1% aqueous formic acid in 25 minutes, MS detection on Agilent MSD 1100A with ESI; Luna 3×250 mm 5 uM C8 column, gradient from 50 to 100% of acetonitrile in 0.1% aqueous formic acid in 25 minutes, MS detection on Agilent MSD 1100SL with APCI. MS data resulting from a positive ion mode ionization (M+1) were used, except those mentioned specifically for a negative ion mode of ionization (M−1). Retention times (r.t.) are given in minutes and were determined by the following LC/MS method: MetaChem Polaris 2×20 mm C18 column, gradient from 2 to 100% of acetonitrile in 0.01% aqueous formic acid in 3.75 min, MS detection on Micromass ZMD with ESI. Yields are given for illustrative purposes only.

Example 1

1-(5-Methanesulfonyl-pyridin-2-yl)-5-(4-methylene-cyclohexylmethoxy)-3-trifluoromethyl-1H-pyrazole-4-carbonitrile 5-Chloro-1-(5-methanesulfonyl-pyridin-2-yl)-3-trifluoromethyl-1H-pyrazole-4-carbonitrile (0.35 g, 1 mmol) and (4-methylene-cyclohexyl)-methanol (0.252 g, 2 mmol) were dissolved in dry dimethylsulfoxide (DMSO) (5 ml) and potassium fluoride (0.116 g, 2 mmol) was added to the clear solution. The resulting mixture was stirred at 20° for a period of 48 hours. Analytical HPLC indicated the reaction completion. The reaction mixture was poured into water (50 ml) and the resulting mixture was extracted with ethyl acetate (20 ml). The organic extract was dried over magnesium sulfate and concentrated with a rotary evaporator. The desired product (0.3 g, 68%) was isolated by chromatography on silica gel eluting with a solution of 15% of ethyl acetate and 15% of acetone in hexane. MS: 440, r.t.: 3.0.

Example 2

5-(2-Fluoro-benzylsulfanyl)-1-(5-methanesulfonyl-pyridin-2-yl)-3-trifluoromethyl-1H-pyrazole-4-carbonitrile 5-Chloro-1-(5-methanesulfonyl-pyridin-2-yl)-3-trifluoromethyl-1H-pyrazole-4-carbonitrile (0.512 g, 1.46 mmol) and (2-fluoro-phenyl)-methanethiol (0.415 g, 2.92 mmol) were dissolved in dry DMSO (5 ml) and cesium fluoride (0.154 g, 2.92 mmol) was added to the clear solution. The resulting mixture was stirred at 20° for a period of 48 hours. Analytical HPLC indicated the reaction completion. The reaction mixture was poured into water (50 ml) and the resulting mixture was extracted with ethyl acetate (20 ml). The organic extract was dried over magnesium sulfate and concentrated with a rotary evaporator. The desired product (0.55 g, 83%) was isolated by chromatography on silica gel eluting with a gradient (from 20–40%) of ethyl acetate in hexane. MS: 457, r.t.: 27, $^1$H-NMR (CDCl$_3$, 400 MHZ) δ 9.05 (d, 1H, H—Ar), 8.44–8.41 (q, 1H, H—Ar), 8.05 (d, 1H, H—Ar), 7.34–7.27 (m, 2H, H—Ar), 7.13–7.02 (m, 2H, H—Ar), 4.61 (s, 2H, CH$_2$ of the benzyl group), 3.16 (s, 3H, CH$_3$ of the CH$_3$SO$_2$ group) ppm.

Example 3

6-[4-cyano-3-difluoromethyl-5-(3,5-cis-dimethyl-piperidin-1-yl)-pyrazol-1-yl]-pyridine-3-sulfonic acid amide 6-(5-Chloro-4-cyano-3-difluoromethyl-pyrazol-1-yl)-pyridine-3-sulfonic acid amide carbonitrile (0.654 g, 1.96 mmol) and 3,5-cis-dimethyl-piperidine hydrochloride (0.587 g, 3.92 mmol) were mixed with dry DMSO (6 ml) and cesium fluoride (0.6 g, 3.92 mmol) was added to the suspension. The resulting mixture was stirred at 20° for a period of 48 hours. Analytical HPLC indicated the reaction completion. The reaction mixture was poured into water (50 ml) and the resulting mixture was extracted with ethyl acetate (20 ml). The organic extract was dried over magnesium sulfate and concentrated with a rotary evaporator. The desired product (0.0.309 g, 38%) was isolated by chromatography on silica gel eluting with a solution of 35% of ethyl acetate in hexane. MS: 410, r.t.: 2.5.

Example 4

6-[4-cyano-5-(2,2-dimethyl-propoxy)-3-trifluoromethyl-pyrazol-1-yl]-pyridine-3-sulfonic acid amide 6-[5-chloro-4-cyano-3-trifluoromethyl-pyrazol-1-yl]-pyridine-3-sulfonic acid dimethyl-aminomethyleneamide (81.3 mg, 0.2 mmol) and 2,2-dimethyl-1-propanol (35.3 mg, 0.4 mmol) were dissolved in dry DMSO (0.5 ml) and cesium fluoride (60.7 mg, 0.4 mmol) was added to the solution. The resulting mixture was stirred at 20° C. for a period of 24 hours. Analytical HPLC indicated the reaction completion. The reaction mixture was poured into water (2 ml) and the resulting mixture was extracted with ethyl acetate (2 ml). The ethyl acetate mixture was filtered into a vial and evaporated to dryness under nitrogen atmosphere to leave a residue. Acetonitrile (2 ml) was added, and the mixture shaken to dissolve the residue. 2N HCl (1.5 ml) was added into the acetonitrile mixture, and the reaction mixture warmed to 70° C. for a period of 18 hours. After cooling down, the acetonitrile was evaporated under reduced pressure, and ethyl acetate (5 ml) was added to the evaporated mixture with stirring. The ethyl acetate layer was then separated, washed with saturated sodium chloride (5 ml), dried over magnesium sulfate and concentrated. HPLC purification of the residue obtained above gives the title compound. (37.6 mg, 46%). MS: 404.5, r.t.: 2.7.

Example 5

3-Difluoromethyl-5-(cis-2,6-dimethyl-morpholin-4-yl)-1-(5-methanesulfonyl-pyridin-2-yl)-1H-pyrazole-4-carbonitrile 5-Chloro-3-difluoromethyl-1-(5-methanesulfonyl-pyridin-2-yl)-1H-pyrazole-4-carbonitrile (1.24 g, 3.7 mmol) and 2,6-cis-dimethylmorpholine (0.86 g, 7.4 mmol) were dissolved in dry dimethylsulfoxide (DMSO) (13 ml) and potassium fluoride (0.43 g, 7.4 mmol) was added to the clear solution. The resulting mixture was stirred at 20° for a period of 2 hours. Analytical HPLC indicated the reaction completion. The reaction mixture was poured into water (50 ml) and the resulting mixture was extracted with ethyl acetate (30 ml). The organic extract was dried over sodium sulfate and concentrated with a rotary evaporator. The desired product (1.3 g, 85%) was isolated by triturating the residue with ether (10 ml) containing 3 drops of methanol, stirring the suspension overnight, filtering, and drying under high vacuum. MS: 412.5, r.t.: 2.2, $^1$HNMR: (in d6-DMSO solvent) 9.02(1H, d, J=2.4), 8.52(1H, dd, J=8.8, 2.8), 7.98 (1H, d, J=8.8), 7.12(1H, t, J=52.8), 3.68(2H, m), 3.36(3H, s), 3.28(2H, m), 2.80(2H, m), 0.99 (6H, d, J=6.4) ppm, $^{13}$C-NMR: (in d6-DMSO solvent) 155.9, 154.2, 148.2, 139.6, 119.2, 113.2, 113.1, 112.0, 109.9, 79.0, 71.6, 55.9, 44.3, 18.9 ppm.

Example 6

5-Cyclopentylamino-3-difluoromethyl-1-(4-methanesulfonyl-phenyl)-1H-pyrazole-4-carbonitrile 5-Chloro-3-difluoromethyl-1-(5-methanesulfonyl-phenyl)-1H-pyrazole-4-carbonitrile (73 mg, 0.22 mmol), cyclopentylamine (18.7 mg, 0.22 mmol), a solution of tetrabutylammonium fluoride in tetrahydrofuran (0.22 ml, 0.22 mmol), and dichloromethane (1 ml) were stirred together at 20° C. for a period of 16 hours. The title compound (41.1 mg, 50%) was isolated by preparative HPLC of the reaction mixture on a normal phase column. MS: 381, r.t.: 2.5.

The chemical structures of the compounds prepared in the above Examples 1 to 6 are summarized in the following Table 2.

TABLE 2

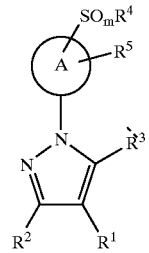

| Ex.# | A | m | R$^1$ | R$^2$ | R$^4$ | R$^5$ | R$^3$ |
|---|---|---|---|---|---|---|---|
| 1 | A2, wherein X is >CH | 2 | CN | CF$_3$ | CH$_3$ | H | —O—CH$_2$-(4-METHYLIDINE-CYCLOHEXYL) |
| 2 | A2, wherein X is >CH | 2 | CN | CF$_3$ | CH$_3$ | H | —S—CH$_2$-(2-FLUORO-PHENYL) |
| 3 | A2, wherein X is >CH | 2 | CN | CHF$_2$ | NH$_2$ | H | CIS-3,5-DI(CH$_3$)PIPERIDIN-1-YL |
| 4 | A2, wherein X is >CH | 2 | CN | CF$_3$ | NH$_2$ | H | —O—CH$_2$—C(CH$_3$)$_2$—CH$_3$ |
| 5 | A2, wherein X is >CH | 2 | CN | CHF$_2$ | CH$_3$ | H | CIS-2,6-DI(CH$_3$)-MORPHOLIN-4-YL |
| 6 | A7 | 2 | CN | CHF$_2$ | CH$_3$ | H | —N-CYCLOPENTYL |

Referring to Table 2, for clarification purposes, Ex.#. is defined as Example number;

—O—CH₂-(4-METHYLIDINE-CYCLOHEXYL) is defined as

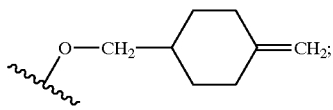

CIS-3,5-DI(CH₃)PIPERIDIN-1-YL is defined as

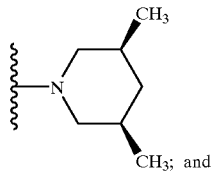

CIS-2,6-DI(CH₃)-MORPHOLIN-4-YL is defined as

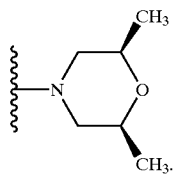

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:
1. A process for preparing a compound of formula I:

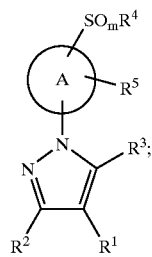

I or a pharmaceutically acceptable salt thereof;
wherein the ring of the formula (R⁵)-A-(SO$_m$R⁴) is selected from the group consisting of

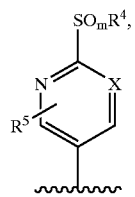

A1

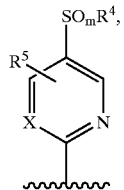

A2

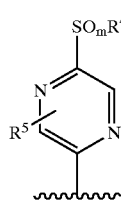

A3

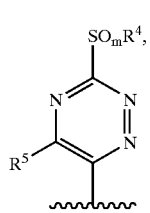

A4

A5

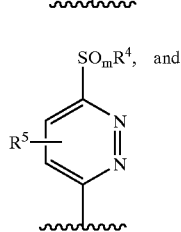

A6, and

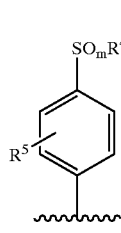

A7 m is 2;

X is >CR⁵;

R¹ is —CN;

R² is a radical selected from the group consisting of H, —NO₂, —CN, (C₂-C₆)alkenyl, (C₂-C₆)alkenyl, (C₃-C₇)cycloalkyl, (C₆-C₁₀)aryl, H—(C=O)—, (C₁-C₆)alkyl-(C=O)—, (C₃-C₇)cycloalkyl-(C=O)—, (C₆-C₁₀)aryl-(C=O)— and (C₁-C₆)alkyl optionally substituted by on —OH group or by one to four fluoro substituents;

$R^3$ is a radical selected from the group consisting of

$R^7$ is a radical independently selected from the group consisting of $C_1$alkyl substituted by one to three substituents of $(C_3-C_7)$ cycloalkyl further substituted on any ring carbon atom by at least one $(C_1-C_6)$alkylidene substituent;

$R^4$ is $(c_1-C_6)$alkyl optionally substituted by one to four —OH substituents; and $R^5$ is H;

comprising reacting a compound of the formula II:

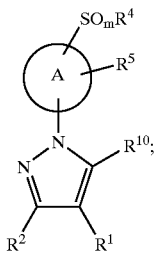

II wherein the ring of the formula $(R^5)$-A-$(SO_mR^4)$, m, and $R^1$ through $R^5$ are as defined above, and wherein $R^{10}$ is a radical selected from the group consisting of halo, $(C_1-C_6)$alkyl-$SO_3$—, $(C_6-C_{10})$aryl-$SO_3$—, $(C_1-C_6)$alkyl-$SO_2$—, and $(C_6-C_{10})$aryl-$SO_2$—, wherein each of said $(C_1-C_6)$alkyl component of said $(C_1-C_6)$alkyl-$SO_3$— and $(C_1-C_6)$alkyl-$SO_2$— radicals is optionally substituted by one to six fluoro substituents;

with a compound of formula $R^3$—H, wherein $R^3$ is as defined above, in the presence of a fluoride containing salt; in the presence of a solvent.

2. The process according to claim 1 wherein said fluoride containing salt contains a cationic metal selected from the group consisting of lithium, sodium, potassium, cesium, magnesium, calcium, strontium, and barium.

3. The process according to claim 2 wherein about 0.05 to about 10 equivalents of said fluoride containing salt relative to the compound of formula I is used.

4. The process according to claim 2 wherein said process is performed at a temperature of about 10° C. to about 30° C.

5. The process according to claim 2 wherein said solvent is dimethylsulfoxide, dimethylformamide, dimethylacetamide, acetone, or acetonitrile.

6. The process according to claim 1 wherein said fluoride containing salt is tetra$(C_1-C_8)$alkylammonium fluoride or $(C_1-C_{16})$alkyltri$(C_1-C_2)$alkylammonium fluoride.

7. The process according to claim 6 wherein 0.1 to 2 equivalents of said fluoride containing salt relative to the compound of formula I is used.

8. The process according to claim 6 wherein said process is performed at a temperature of about 20° C. to about 80° C.

9. The process according to claim 6 wherein said solvent is acetonitrile, dichloromethane, chloroform, tetrahydrofuran, or dichloroethane.

10. The process according to claim 1 wherein $R^{10}$ is chloro.

11. The process according to claim 1 wherein $R^{10}$ is $CF_3$—$SO_3$— or $CF_3CF_2$—$SO_3$—.

12. The process according to claim 1 wherein $R^2$ is a radical selected from the group consisting of H, —$NO_2$, —CN, and $(C_1-C_6)$alkyl optionally substituted by one —OH or by one to three fluoro substituents.

13. The process according to claim 1 wherein $R^2$ is —$CF_3$ or —$CHF_2$.

14. The process according to claim 1 wherein the ring of the formula $(R^5)$-A-$(SO_mR^4)$ is of the formula

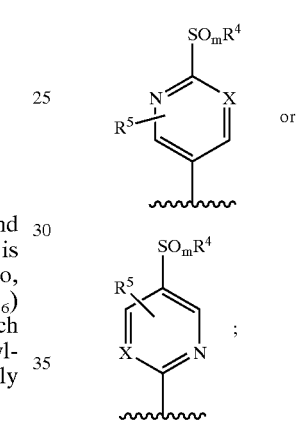

wherein X is >CH and m is 2.

15. The process according to claim 1 wherein $R^1$ is —CN.

16. The process according to claim 1 wherein $R^4$ is $(C_1-C_6)$alkyl optionally substituted by one to four —OH substituents.

17. The process according to claim 1 wherein the ring of the formula $(R^5)$-A-$(SO_mR^4)$ is of the formula

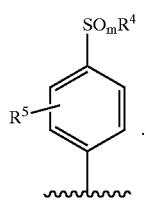

A7

* * * * *